(12) United States Patent
Hickey et al.

(10) Patent No.: US 9,527,895 B2
(45) Date of Patent: *Dec. 27, 2016

(54) CAPCNA PEPTIDE THERAPEUTICS FOR CANCER

(71) Applicants: Robert J. Hickey, Indianapolis, IN (US); Linda H. Malkas, Indianapolis, IN (US)

(72) Inventors: Robert J. Hickey, Indianapolis, IN (US); Linda H. Malkas, Indianapolis, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/045,223

(22) Filed: Oct. 3, 2013

(65) Prior Publication Data

US 2014/0212510 A1 Jul. 31, 2014

Related U.S. Application Data

(63) Continuation of application No. 13/500,597, filed as application No. PCT/US2010/051843 on Oct. 7, 2010, now abandoned.

(60) Provisional application No. 61/249,528, filed on Oct. 7, 2009.

(51) Int. Cl.
| | |
|---|---|
| *A61K 38/08* | (2006.01) |
| *C07K 7/06* | (2006.01) |
| *A61P 35/00* | (2006.01) |
| *C07K 14/47* | (2006.01) |
| *A61K 45/06* | (2006.01) |
| *A61K 38/10* | (2006.01) |
| *A61K 38/17* | (2006.01) |
| *A61K 33/24* | (2006.01) |

(52) U.S. Cl.
CPC .......... *C07K 14/4738* (2013.01); *A61K 33/24* (2013.01); *A61K 38/08* (2013.01); *A61K 38/10* (2013.01); *A61K 38/1709* (2013.01); *A61K 45/06* (2013.01)

(58) Field of Classification Search
CPC .... A61K 38/08; A61K 45/06; A61K 2300/00; A61K 33/24; A61K 38/10; A61K 38/1709; C07K 14/4738
See application file for complete search history.

(56) References Cited

U.S. PATENT DOCUMENTS 5,595,756 A * 1/1997 Bally et al. ........... 424/450

FOREIGN PATENT DOCUMENTS

WO    WO 2007/098415 A2 *    8/2007    .............. C07K 7/00

OTHER PUBLICATIONS

Strzalka et al, Molecular cloning of Phaseolus vulgaris cDNA encoding proliferating cell nuclear antigen, Journal of Plant Physiology, 2007, 164, pp. 209-213.*
Sporn, B and Suh, N, Chemoprevention of cancer, Carcinogenesis, 2000, 21, pp. 525-530.*
Auerbach. R. et al, Angiogenesis assays: Problems and pitfalls, Cancer and Metastasis Reviews, 2000, 19, pp. 167-172.*
Gura, T. Systems for Identifying New Drugs are Often Faulty, Science, 1997, 278, pp. 1041-1042.*
Jain R. K., Barriers to Drug Delivery in Solid Tumors, Scientific American, 1994, pp. 58-65.*
Cancer Drug Design and Discovery. Neidle, Stephen, ed., Elsevier/ACademic Press, 2008, p. 427-431.*
Zhong et al, Association of BRCA1 with the hRad50-hMre11-p95 Complex and the DNA Damage Response, Science, 1999, 285, pp. 747-750.*
Ragin et al, Cellular Import Mediated by Nuclear Localization Signal Peptide Sequences, Chemistry & Biology, 2002, 8, pp. 943-948.*
Goldberg et al, Intratumoral cancer chemotherapy and immunotherapy: opportunities for nonsystemic preoperative drug delivery, JPP, 2002, 54, pp. 159-180.*
Ball et al, Human and plant proliferating-cell nuclear antigen have a highly conserved binding site for the p53-inducible gene product p21WAF1, Eur. J. Biochem., 1996, 237, pp. 854-861.*
Fischer, Cellular Uptake Mechanisms and Potential Therapeutic Utility of Peptidic Cell Delivery Vectors: Progress 2001-2006, Medicinal Research Reviews, 2007, 27, pp. 755-795.*
Ross et al, HER-2/neu Testing in Breast Cancer, Am J Clin Pathol, 2003, 120, pp. S53-S71.*
Different types of chemotherapy drugs, from http://www.cancer.org/treatment/treatmentsandsideeffects/treatmenttypes/chemotherapy/ch . . . , pp. 1-5, accessed Aug. 26, 2014.*
DNA repair proteins, from New England BioLabs Inc., p. 1, accessed Dec. 14, 2014.*

* cited by examiner

*Primary Examiner* — Julie Ha
*Assistant Examiner* — Li Ni Komatsu
(74) *Attorney, Agent, or Firm* — Whiteford, Taylor & Preston, LLP; Peter J. Davis

(57) ABSTRACT

Administration of compositions comprising cell-permeable cancer-specific proliferating cell nuclear antigen derived peptides and their variants reduces the proliferation of cancer cells and also augments cytotoxic effects of chemotherapeutics. The compositions are effective in cells harboring mutations in DNA repair proteins.

15 Claims, 10 Drawing Sheets

SEQUENCE LISTING

```
<160> NUMBER OF SEQ ID NOS: 86

<210> SEQ ID NO 1
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 1

Leu Gly Ile Pro Glu Gln Glu Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 2

Leu Ala Ile Pro Glu Gln Glu Tyr
1               5

<210> SEQ ID NO 3
<211> LENGTH: 8
```

-continued

```
<212> TYPE: PRT
<213> ORGANISM: Artificial Sequence
<220> FEATURE:
<223> OTHER INFORMATION: Synthetic Peptide

<400> SEQUENCE: 3

Leu Gly Ile Ala Glu Gln Glu Tyr
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 4

Leu Gly Ile Pro Ala Gln Glu Tyr
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 5

Leu Gly Ile Pro Glu Ala Glu Tyr
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 6

Leu Gly Ile Pro Glu Gln Ala Tyr
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 7

Leu Gly Ile Ala Glu Ala Glu Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 8

Leu Gly Ile Pro Glu Ala Ala Tyr
1               5

<210> SEQ ID NO 9
<211> LENGTH: 8
<212> TYPE: PRT
```

```
<213> ORGANISM: Artificial Sequence
<220> FEATURE:
<223> OTHER INFORMATION: Synthetic Peptide

<400> SEQUENCE: 9

Leu Gly Ile Ala Glu Gln Ala Tyr
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 10

Leu Gly Ile Ala Glu Ala Ala Tyr
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 11

Arg Arg Arg Arg Arg Arg Arg
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 12

Arg Arg Arg Arg Arg Arg Arg Arg
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 13

Arg Arg Arg Arg Arg Arg Arg Arg Arg
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 14

Arg Arg Arg Arg Arg Arg Arg Arg Arg Arg
1               5                   10

<210> SEQ ID NO 15
<211> LENGTH: 11
<212> TYPE: PRT
<213> ORGANISM: Artificial Sequence
```

```
<220> FEATURE:
<223> OTHER INFORMATION: Synthetic Peptide

<400> SEQUENCE: 15

Arg Arg Arg Arg Arg Arg Arg Arg Arg Arg
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 16

Arg Gln Ile Lys Ile Trp Phe Gln Asn Arg Arg Met Lys Trp Lys Lys
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 17

Gly Arg Lys Lys Arg Arg Gln Arg Arg Arg Pro Pro Gln
1               5                   10

<210> SEQ ID NO 18
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 18

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 19
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 19

Gly Arg Lys Lys Arg Arg Gln Arg Arg Arg
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 20

Arg Arg Arg Arg Arg Arg Arg Arg Arg Leu Gly Ile Pro Glu Gln Glu
1               5                   10                  15

Tyr
```

```
<210> SEQ ID NO 21
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 21

Gln Leu Gly Ile Pro Glu Gln Glu Tyr Ser Cys
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 22

Val Glu Gln Leu Gly Ile Pro Glu Gln Glu Tyr
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 23

Leu Gly Ile Pro Glu Gln Glu Tyr Ser Cys Val Val Lys
1               5                   10

<210> SEQ ID NO 24
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 24

Leu Gly Ile Pro Glu Gln Glu Tyr Ser Cys Val Val Lys Met Pro Ser
1               5                   10                  15

Gly

<210> SEQ ID NO 25
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 25

Glu Gln Leu Gly Ile Pro Glu Gln Glu Tyr
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 26

Gln Leu Gly Ile Pro Glu Gln Glu Tyr
1               5
```

<210> SEQ ID NO 27
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 27

Leu Gly Ile Pro Glu Gln Glu Tyr Ser Cys Val Val Lys Met Pro Ser
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 28

Leu Gly Ile Pro Glu Gln Glu Tyr Ser Cys Val Val Lys Met Pro
1               5                   10                  15

<210> SEQ ID NO 29
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 29

Leu Gly Ile Pro Glu Gln Glu Tyr Ser Cys Val Val Lys Met
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 30

Leu Gly Ile Pro Glu Gln Glu Tyr Ser Cys Val Val
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 31

Leu Gly Ile Pro Glu Gln Glu Tyr Ser Cys Val
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 32

Leu Gly Ile Pro Glu Gln Glu Tyr Ser Cys
1               5                   10

```
<210> SEQ ID NO 33
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 33

Gln Leu Gly Ile Pro Glu Gln Glu Tyr Ser Cys
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 34

Leu Gly Ile Pro Glu Gln Glu Tyr Ser
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(8)
<223> OTHER INFORMATION: "See specification as filed for detailed
      description of substitutions and preferred embodiments"
<220> FEATURE:
<221> NAME/KEY: MOD_RES
<222> LOCATION: (2)..(2)
<223> OTHER INFORMATION: any amino acid
<220> FEATURE:
<221> NAME/KEY: MOD_RES
<222> LOCATION: (4)..(4)
<223> OTHER INFORMATION: any amino acid
<220> FEATURE:
<221> NAME/KEY: MOD_RES
<222> LOCATION: (6)..(7)
<223> OTHER INFORMATION: any amino acid

<400> SEQUENCE: 35

Leu Xaa Ile Xaa Glu Xaa Xaa Tyr
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 36

His Ala Ile Tyr Pro Arg His
1               5

<210> SEQ ID NO 37
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 37

Thr His Arg Pro Pro Met Trp Ser Pro Val Trp Pro
```

```
1               5                   10

<210> SEQ ID NO 38
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 38

Arg Tyr Ile Arg Ser
1               5

<210> SEQ ID NO 39
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 39

Val Gln Arg Lys Arg Gln Lys Leu Met Pro
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 40

Ser Lys Lys Lys Lys Ile Lys Val
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 41

Gly Arg Lys Arg Lys Lys Arg Thr
1               5

<210> SEQ ID NO 42
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 42

Val Ser Asp Tyr Glu Met Lys Leu Met Asp Leu Asp Val Glu Gln
1               5                   10                  15

<210> SEQ ID NO 43
<211> LENGTH: 100
<212> TYPE: PRT
<213> ORGANISM: Artificial Sequence
<220> FEATURE:
<223> OTHER INFORMATION: Synthetic Peptide

<400> SEQUENCE: 43

Leu Val Phe Glu Ala Pro Asn Gln Glu Lys Val Ser Asp Tyr Glu Met
1               5                   10                  15
```

-continued

Lys Leu Met Asp Leu Asp Val Glu Gln Leu Gly Ile Pro Glu Gln Glu
            20                  25                  30

Tyr Ser Cys Val Val Lys Met Pro Ser Gly Glu Phe Ala Arg Ile Cys
        35                  40                  45

Arg Asp Leu Ser His Ile Gly Asp Ala Val Val Ile Ser Cys Ala Lys
 50                  55                  60

Asp Gly Val Lys Phe Ser Ala Ser Gly Glu Leu Gly Asn Gly Asn Ile
65                  70                  75                  80

Lys Leu Ser Gln Thr Ser Asn Val Asp Lys Glu Glu Ala Val Thr
                85                  90                  95

Ile Glu Met Asn
        100

<210> SEQ ID NO 44
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 44

Leu Met Asp Leu Asp Val Glu Gln Leu Gly Ile Pro Glu Gln Glu Tyr
1               5                   10                  15

Ser Cys

<210> SEQ ID NO 45
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 45

Asp Val Glu Gln Leu Gly Ile Pro Glu Gln Glu Tyr
1               5                   10

<210> SEQ ID NO 46
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 46

Leu Gly Ile Pro Glu Gln Glu Tyr Ser Cys Val Val Lys Met Pro Ser
1               5                   10                  15

Gly Glu

<210> SEQ ID NO 47
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 47

Leu Gly Ile Pro Glu Gln Glu Tyr Ser Cys Val Val Lys Met Pro Ser
1               5                   10                  15

Gly Glu Phe Ala Arg Ile Cys Arg Asp Leu Ser His
            20                  25

```
<210> SEQ ID NO 48
<211> LENGTH: 38
<212> TYPE: PRT
<213> ORGANISM: Artificial Sequence
<220> FEATURE:
<223> OTHER INFORMATION: Synthetic Peptide

<400> SEQUENCE: 48

Leu Gly Ile Pro Glu Gln Glu Tyr Ser Cys Val Val Lys Met Pro Ser
1               5                   10                  15

Gly Glu Phe Ala Arg Ile Cys Arg Asp Leu Ser His Ile Gly Asp Ala
            20                  25                  30

Val Val Ile Ser Cys Ala
        35

<210> SEQ ID NO 49
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 49

Arg Arg Arg Arg Arg Arg Arg Arg Cys Cys Leu Gly Ile Pro Glu
1               5                   10                  15

Gln Glu Tyr

<210> SEQ ID NO 50
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 50

Arg Arg Arg Arg Arg Arg Arg Arg Cys Cys Ala Gly Ile Pro Glu
1               5                   10                  15

Gln Glu Tyr

<210> SEQ ID NO 51
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 51

Arg Arg Arg Arg Arg Arg Arg Arg Cys Cys Leu Ala Ile Pro Glu
1               5                   10                  15

Gln Glu Tyr

<210> SEQ ID NO 52
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 52

Arg Arg Arg Arg Arg Arg Arg Arg Cys Cys Leu Gly Ala Pro Glu
1               5                   10                  15

Gln Glu Tyr
```

-continued

<210> SEQ ID NO 53
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 53

Arg Arg Arg Arg Arg Arg Arg Arg Arg Cys Cys Leu Gly Ile Ala Glu
1               5                   10                  15

Gln Glu Tyr

<210> SEQ ID NO 54
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 54

Arg Arg Arg Arg Arg Arg Arg Arg Arg Cys Cys Leu Gly Ile Pro Ala
1               5                   10                  15

Gln Glu Tyr

<210> SEQ ID NO 55
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 55

Arg Arg Arg Arg Arg Arg Arg Arg Arg Cys Cys Leu Gly Ile Pro Glu
1               5                   10                  15

Ala Glu Tyr

<210> SEQ ID NO 56
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 56

Arg Arg Arg Arg Arg Arg Arg Arg Arg Cys Cys Leu Gly Ile Pro Glu
1               5                   10                  15

Gln Ala Tyr

<210> SEQ ID NO 57
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 57

Arg Arg Arg Arg Arg Arg Arg Arg Arg Cys Cys Leu Gly Ile Pro Glu
1               5                   10                  15

Gln Glu Ala

<210> SEQ ID NO 58
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 58

Arg Arg Arg Arg Arg Arg Arg Arg Arg Leu Gly Ile Pro Glu Gln Glu
1               5                   10                  15

Tyr

<210> SEQ ID NO 59
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 59

Arg Arg Arg Arg Arg Arg Arg Arg Arg Ala Gly Ile Pro Glu Gln Glu
1               5                   10                  15

Tyr

<210> SEQ ID NO 60
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 60

Arg Arg Arg Arg Arg Arg Arg Arg Arg Leu Ala Ile Pro Glu Gln Glu
1               5                   10                  15

Tyr

<210> SEQ ID NO 61
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 61

Arg Arg Arg Arg Arg Arg Arg Arg Arg Leu Gly Ala Pro Glu Gln Glu
1               5                   10                  15

Tyr

<210> SEQ ID NO 62
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 62

Arg Arg Arg Arg Arg Arg Arg Arg Arg Leu Gly Ile Ala Glu Gln Glu
1               5                   10                  15

Tyr

<210> SEQ ID NO 63
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 63

```
Arg Arg Arg Arg Arg Arg Arg Arg Arg Leu Gly Ile Pro Ala Gln Glu
1               5                   10                  15

Tyr
```

<210> SEQ ID NO 64
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 64

```
Arg Arg Arg Arg Arg Arg Arg Arg Arg Leu Gly Ile Pro Glu Ala Glu
1               5                   10                  15

Tyr
```

<210> SEQ ID NO 65
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 65

```
Arg Arg Arg Arg Arg Arg Arg Arg Arg Leu Gly Ile Pro Glu Gln Ala
1               5                   10                  15

Tyr
```

<210> SEQ ID NO 66
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 66

```
Arg Arg Arg Arg Arg Arg Arg Arg Arg Leu Gly Ile Pro Glu Gln Glu
1               5                   10                  15

Ala
```

<210> SEQ ID NO 67
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 67

```
Tyr Gly Arg Lys Lys Arg Arg Gln Arg Arg
1               5                   10
```

<210> SEQ ID NO 68
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (15)..(15)
<223> OTHER INFORMATION: Cys(S-3-nitro-2-pyridinesulfenyl)

<400> SEQUENCE: 68

```
Tyr Gly Arg Lys Lys Arg Arg Gln Arg Arg Arg Gly Gly Gly Cys
```

<210> SEQ ID NO 69
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 69

Asp Ala Ala Thr Ala Thr Arg Gly Arg Ser Ala Ser Arg Pro Thr
1               5                   10                  15

Glu Arg Pro Arg Ala Pro Ala Arg Ser Ala Ser Arg Pro Arg Arg Pro
            20                  25                  30

Val Asp

<210> SEQ ID NO 70
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 70

Lys Leu Ala Leu Lys Leu Ala Leu Lys Ala Leu Lys Ala Ala Leu Lys
1               5                   10                  15

Leu Ala

<210> SEQ ID NO 71
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 71

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 72
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 72

Gly Leu Phe Arg Ala Leu Leu Arg Leu Leu Arg Ser Leu Trp Arg Leu
1               5                   10                  15

Leu Leu Arg Ala
            20

<210> SEQ ID NO 73
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 73

Val Arg Leu Pro Pro Pro
1               5

<210> SEQ ID NO 74
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 74

Met Gly Leu Gly Leu His Leu Leu Val Leu Ala Ala Leu Gln Gly
1               5                   10                  15

Ala Trp Ser Gln Pro Lys Lys Lys Arg Lys Val
            20                  25

<210> SEQ ID NO 75
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 75

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 76
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 76

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 77
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 77

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 78
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 78

Cys Ser Ile Pro Pro Glu Val Lys Phe Asn Lys Pro Phe Val Tyr Leu
1               5                   10                  15

Ile

<210> SEQ ID NO 79
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 79

Ser Ile Pro Pro Glu Val Lys Phe Asn Lys Pro Phe Val Tyr Leu Ile
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 80

Lys Lys Ala Ala Ala Val Leu Leu Pro Val Leu Leu Ala Ala Pro
1               5                   10                  15

<210> SEQ ID NO 81
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 81

Pro Lys Lys Lys Arg Lys Val
1               5

<210> SEQ ID NO 82
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 82

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly Gly Gly Gly
                20                  25                  30

<210> SEQ ID NO 83
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 83

Ala Cys Ser Ser Ser Pro Ser Lys His Cys Gly
1               5                   10

<210> SEQ ID NO 84
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 84

```
Lys Lys Trp Lys Met Arg Arg Asn Gln Phe Trp Val Lys Val Gln Arg
1               5                   10                  15

Gly

<210> SEQ ID NO 85
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 85

Arg Gln Ile Lys Ile Trp Phe Gln Asn Arg Arg Met Lys Trp Lys Lys
1               5                   10                  15

<210> SEQ ID NO 86
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 86

Arg Gly Gly Arg Leu Ser Tyr Ser Arg Arg Phe Ser Thr Ser Thr
1               5                   10                  15

Gly Arg Ala
```

CAPCNA PEPTIDE THERAPEUTICS FOR CANCER

CROSS REFERENCE TO RELATED APPLICATIONS

This application is a continuation application of U.S. application Ser. No. 13/500,597, which is a U.S. national counterpart application of international application serial No. PCT/US2010/051843 filed Oct. 7, 2010, which claims priority under 35 USC §119(e) to U.S. Provisional Application Ser. No. 61/249,528 filed on Oct. 7, 2009. The entire disclosures of U.S. Ser. No. 13/500,597, PCT/US2010/051843, and U.S. Ser. No. 61/249,528 are hereby incorporated by reference.

GOVERNMENT RIGHTS

This invention was made with government support under CA121289 awarded by the National Institutes of Health and W81XWH-07-1-0707 awarded by the Department of Defense. The U.S. Government has certain rights in the invention.

INCORPORATION OF SEQUENCE LISTING

The sequence listing with file name 213944_ST25.txt, created on Oct. 7, 2010 (21.8 KB) is expressly incorporated by reference in its entirety.

TECHNICAL FIELD

This disclosure relates to peptide-based therapeutic compositions and methods to inhibit cancer cell proliferation.

BACKGROUND

Proliferating cell nuclear antigen (PCNA) plays an important role in the process of DNA replication, repair, chromosomal recombination, cell cycle check-point control and other cellular proliferative activities. In conjunction with an adaptor protein, replication factor C(RFC), PCNA forms a moving clamp that is the docking point for DNA polymerases delta and epsilon. Different isoforms of proliferating cell nuclear antigen (PCNA) that display both acidic and basic isoelectric points (pI) have been demonstrated. Analysis of PCNA by two-dimensional polyacrylamide gel electrophoresis (2D PAGE) from both malignant and non-malignant breast cells (referred to as non-malignant PCNA or nmPCNA) and tissues revealed the presence of an acidic form of PCNA only in malignant cells (referred to as the cancer-specific PCNA or csPCNA or caPCNA). This difference in isoelectric points between these two forms of PCNA appears to result from an alteration in the ability of the malignant cells to post-translationally modify the PCNA polypeptide and is not due to a genetic change within the PCNA gene.

Structural work examining the structure of the PCNA polypeptide to define the structural differences between the caPCNA and non-malignant cell isoform of PCNA revealed a region of the caPCNA protein that is uniquely exposed only in the cancer cell. An antibody was developed to a region of the cancer specific isoform of PCNA that is highly selective for the PCNA isoform expressed exclusively in cancer cells.

Proliferating cell nuclear antigen (PCNA) is a 29 kDa nuclear protein and its expression in cells during the S and G2 phases of the cell cycle makes the protein a good cell proliferation marker. It has also been shown to partner in many of the molecular pathways responsible for the life and death of the cell. Its periodic appearance in S phase nuclei suggested an involvement in DNA replication. PCNA was later identified as a DNA polymerase accessory factor in mammalian cells and an essential factor for SV40 DNA replication in vitro. In addition to functioning as a DNA sliding clamp protein and a DNA polymerase accessory factor in mammalian cells, PCNA interacts with a number of other proteins involved in transcription, cell cycle checkpoints, chromatin remodeling, recombination, apoptosis, and other forms of DNA repair. Besides being diverse in action, PCNA's many binding partners are linked by their contributions to the precise inheritance of cellular functions by each new generation of cells. PCNA may act as a master molecule that coordinates chromosome processing.

PCNA is also known to interact with other factors like FEN-1, DNA ligase, and DNA methyl transferase. Additionally, PCNA was also shown to be an essential player in multiple DNA repair pathways. Interactions with proteins like the mismatch recognition protein, Msh2, and the nucleotide excision repair endonuclease, XPG, have implicated PCNA in processes distinct from DNA synthesis. Interactions with multiple partners generally rely on mechanisms that enable PCNA to selectively interact in an ordered and energetically favorable way.

The use of short synthetic peptides for the generation of polyclonal and monoclonal antibodies has been successful. Peptides are known to serve as chemo-attractants, potent neurological and respiratory toxins, and hormones. The peptides have also been used as affinity targets and probes for biochemical studies, and have provided a basis for understanding the characteristics and specific nature of discrete protein-protein interactions. In addition, peptide hormones exert potent physiological effects, and in some cases the active hormone is either a peptide that is contained within a larger protein or is processed and released from a precursor protein prior to exerting its physiological effect.

Peptides have been used to disrupt protein-protein interactions, by acting as highly specific competitors of these interactions. Biochemical studies employing peptide reagents advanced the use of peptides as therapeutic drugs capable of disrupting cell functions that require protein-protein interactions. Thus, specific cellular processes such as apoptosis and cell cycle progression, which are dependent upon discrete protein-protein interactions, can be inhibited if these protein-protein interactions are selectively disrupted. The replication of genomic DNA being dependent on protein-protein interactions is also susceptible to peptide-induced inhibition of these protein interactions.

In vivo DNA synthesis is a highly regulated process that depends on a myriad of biochemical reactions mediated by a complex series of protein-protein interactions. Cell division is dependent on the DNA synthetic process, and cancer cell growth is substantially sensitive to any agent that disrupts the regulation and/or the activity of the DNA synthetic machinery responsible for copying the cancer cell's genomic DNA. In addition, it was demonstrated that one signature of cancer, for example, breast cancer, is the induction of genomic instability, as transformed cells develop a highly aggressive metastatic phenotype. Genomic instability arises through a series of changes in the cellular DNA synthetic machinery that alters the fidelity with which DNA is synthesized.

Studies utilizing the carboxyl terminal 26 amino acids from the p21cip protein, (which is known to interact with the PCNA protein), demonstrated the ability of this peptide to disrupt the cellular proliferative process. This peptide fragment of p21 potentially disrupts one or more cellular processes utilizing PCNA and presumably interferes with protein-protein interactions that participate in the DNA synthetic process as well as the regulation of other cell cycle check-point controls and the induction of apoptosis.

Studies utilizing this peptide fragment of p21 have demonstrated the ability of the p21 peptide to activate a non-caspase associated apoptotic pathway. Similarly, studies involving a 39 amino acid peptide fragment of the p21 protein partially inhibited DNA replication in vivo, and suggest that this peptide fragment of p21 can stabilize the PCNA-p21 protein interaction leading to the decrease in DNA synthetic activity within the cell.

In addition, computational chemical methods are being used to model specific regions of the PCNA molecule that may interact with other cellular proteins involved in cell cycle check point control and DNA synthesis. Regions of the cyclin-CDK complex may serve as templates to identify target sites for disrupting key cell cycle check-point control points that are essential for cell proliferation.

Use of synthetic peptides to inhibit cell proliferation and the process of selectively targeting cancer specific PCNA protein to mediate the inhibition of cell proliferation is needed to treat cancer. Peptidomimetic drugs that interact with an antigenic site or target site on caPCNA to disrupt specific protein-caPCNA interactions that are unique to the cancer cell are desired. Peptides derived from caPCNA specific epitopes, described herein, significantly augment the cytotoxic effects of standard chemotherapeutic regimens and consequently kill cancer cells in a highly selective manner.

Germ-line mutations in BRCA1 or BRCA2 alleles are associated with a high risk of the development of a number of cancers, including breast, ovarian, and prostate cancer. Cells lacking these or other important DNA repair proteins have deficiencies in the repair of DNA double stranded breaks by homologous recombination. For example, loss of BRCA1 function often leads to aggressive tumors, and the tumors are often resistant to chemotherapeutic DNA damaging agents. Thus, novel therapeutics, such as caPCNA peptides, that exploit the DNA repair defects in cancers harboring mutations in homologous recombination pathways, are advantageous to standard chemotherapeutics used alone.

SUMMARY

A method of inducing cell death in a cancer cell or a pre-malignant cell includes administering a therapeutically effective amount of a composition comprising a caPCNA peptide, wherein the caPCNA peptide comprises an amino acid sequence selected from LGIPEQEY (SEQ ID NO: 1), LAIPEQEY (SEQ ID NO: 2), LGIAEQEY (SEQ ID NO: 3), LGIPAQEY (SEQ ID NO: 4), LGIPEAEY (SEQ ID NO: 5), LGIPEQAY (SEQ ID NO: 6), LGIAEAEY (SEQ ID NO: 7), LGIPEAAY (SEQ ID NO: 8), LGIAEQAY (SEQ ID NO: 9), and LGIAEAAY (SEQ ID NO: 10).

In an aspect, the cell harbors one or more mutations in a DNA repair protein. In an aspect, the DNA repair protein participates in homologous recombination. Illustrative examples of homologous recombination repair proteins include, but are not limited to BRCA1, BRCA2, or PALB2, RAD51, RAD52, XRCC3, MRE11, and the like. Illustratively, the cancer cell or pre-malignant cell may be a breast, ovarian, or prostate cell.

A method of reducing cellular proliferation of a cancer cell or a pre-malignant cell of an individual having one or more mutations in a DNA repair protein includes administering a therapeutically effective amount of a composition comprising a caPCNA peptide. Amino acid substitutions in one or more positions of a caPCNA peptide improve the cytotoxic effects of caPCNA-derived peptides. caPCNA-derived peptides, including amino acid substituted peptides that have tags or domains that enhance cellular uptake, increase the cytotoxic effects of the caPCNA peptides.

A method of reducing cellular proliferation of malignant cells harboring a mutation of a DNA repair protein includes administering a composition comprising a peptide molecule, the peptide molecule having an amino acid sequence selected from LGIPEQEY (SEQ ID NO: 1), LAIPEQEY (SEQ ID NO: 2), LGIAEQEY (SEQ ID NO: 3), LGIPAQEY (SEQ ID NO: 4), LGIPEAEY (SEQ ID NO: 5), LGIPEQAY (SEQ ID NO: 6), LGIAEAEY (SEQ ID NO: 7), LGIPEAAY (SEQ ID NO: 8), LGIAEQAY (SEQ ID NO: 9), and LGIAEAAY (SEQ ID NO: 10). In an embodiment, the peptide molecule is a synthetic molecule.

A method of reducing proliferation and/or inducing cell death in a cancer cell harboring a mutation of a DNA repair protein includes administering a composition comprising a peptide molecule, the peptide molecule consisting essentially of an amino acid sequence selected from LGIPEQEY (SEQ ID NO: 1), LAIPEQEY (SEQ ID NO: 2), LGIAEQEY (SEQ ID NO: 3), LGIPAQEY (SEQ ID NO: 4), LGIPEAEY (SEQ ID NO: 5), LGIPEQAY (SEQ ID NO: 6), LGIAEAEY (SEQ ID NO: 7), LGIPEAAY (SEQ ID NO: 8), LGIAEQAY (SEQ ID NO: 9), and LGIAEAAY (SEQ ID NO: 10).

In an embodiment, the caPCNA-derived peptide molecules further include a cell permeable factor or a cell-uptake agent. For example, the cell-permeable factor is a cell penetrating peptide selected from amino acid sequences RRRRRRR (SEQ ID NO: 11), RRRRRRRR (SEQ ID NO: 12), RRRRRRRRR (SEQ ID NO: 13), RRRRRRRRRR (SEQ ID NO: 14), RRRRRRRRRRR (SEQ ID NO: 15), RQIKIWFQNRRMKWKK (SEQ ID NO: 16), GRKKRRQRRRPPQ (SEQ ID NO: 17), GWTLNSAGYLLG-KINLKALAALAKKIL (SEQ ID NO: 18), GRKKRRQRRR (SEQ ID NO: 19) or a factor listed in Table 4. In some aspects, the cell penetrating peptide includes one or more D-amino acids. Illustratively, the cell penetrating peptide may comprise 1, 2, 3, 4, 5, 6, 7, 8, 9, 10, 11 or more D-Arg residues. In some aspects, the cell penetrating peptide is covalently linked or conjugated to the peptide molecules derived from caPCNA. In other aspects, the cell penetrating peptide is recombinantly fused with the peptide molecule.

In an embodiment, suitable cell surface targeting factors may be used along with one or more of the compositions disclosed herein. Illustrative examples of cell surface targeting factors include HER2/neu, estrogen receptor, progesterone receptor, epidermal growth factor receptor (EGFR), and the like.

In an embodiment, nuclear localization sequences (NLS) may be used to transport the peptides and/or peptide variants disclosed herein to their targets in tumor cells.

In an embodiment, the cell penetrating peptides may further include a spacer sequence. The spacer sequence may be about 1-10 or about 1-20 amino acids in length. Synthetic spacers are also suitable as long as they do not interfere with the translocation of the peptide across the cell membrane.

In an embodiment, the peptide is engineered to be protease resistant compared to an unmodified native caPCNA-derived peptide. In an embodiment, the peptides disclosed herein are generated as retro-inverso isomers.

It is appreciated herein that the therapeutic compositions may contain one or more caPCNA derived peptides and/or variants, nuclear localization sequences, cell penetrating peptides, spacers, or any combination thereof.

In an embodiment, the administration of a composition that includes a caPCNA-derived translocatable peptide further includes administration of a chemotherapeutic agent. Preferably, the chemotherapeutic agent is a DNA damaging agent. Illustrative examples of DNA damaging agents include doxorubicin, irinotecan, cyclophosphamide, chlorambucil, melphalan, methotrexate, cytarabine, fludarabine, 6-mercaptopurine, 5-fluorouracil, capecytabine, cisplatin, carboplatin, oxaliplatin, and/or combinations thereof. It is appreciated herein that chemotherapeutic agent may be administered to a cancer patient prior to, along with, or after the administration of the composition that includes the caPCNA-derived peptides or variants thereof. It is also appreciated that one or more chemotherapeutic agents may be formulated together with one or more caPCNA peptides. In an embodiment, the compositions that include the caPCNA peptides may be delivered as a liposome. In an aspect, one or more constituents of the pharmaceutical composition that includes caPCNA-derived peptides may further include nanoparticles.

In an embodiment, a composition comprising caPCNA-derived peptides is administered intravenously. It is appreciated herein that any mode of administration, including direct delivery to pre-malignant, cancer, or tumor cells or tissue is possible. In an embodiment, radiotherapy may also be administered prior to or along with or after the administration of the composition that includes the caPCNA-derived peptides or variants thereof. Radio therapy includes, for example, beam radiation therapy and radioisotope therapy.

Rational drug design methodologies can also be implemented to obtain specific inhibitors of caPCNA cellular interaction based on the structural or sequence information of a caPCNA derived peptide, e.g., a peptide that has an amino acid sequence LGIPEQEY (SEQ ID NO: 1). In an embodiment, the agent is a peptide fragment derived from an intracellular protein. In an embodiment, the intracellular protein is known to interact with caPCNA.

A therapeutic composition for reducing in vivo cellular proliferation of malignant cells that express a cancer specific isoform of proliferating cell nuclear antigen (caPCNA), wherein the cells harbor a mutation in a DNA repair protein is described. The composition includes a peptide molecule that has an amino acid sequence LGIPEQEY (SEQ ID NO: 1) with a cell-permeable peptide sequence comprising a polyarginine sequence. In an embodiment, the peptide domain that facilitates peptide uptake across cells is R9 (SEQ ID NO: 13) (nonarginine tag).

A method for reducing in vivo cellular proliferation of malignant cells that express a cancer specific isoform of proliferating cell nuclear antigen (caPCNA), wherein the cells harbor a mutation of a DNA repair protein, comprises administering a composition comprising a peptide molecule, the peptide molecule comprising an amino acid sequence R9-LGIPEQEY (SEQ ID NO: 20) with one or more amino acid substitutions or a functionally equivalent structure thereof or a peptidomimetic thereof, wherein R9 is either conjugated chemically or is part of a recombinant fusion protein.

Other caPCNA-derived peptide inhibitors suitable for use in the methods described herein include caPCNA peptides wherein one or more amino acids are substituted include QLGIPEQEYSC (SEQ ID NO: 21), VEQLGIPEQEY (SEQ ID NO: 22), LGIPEQEYSCVVK (SEQ ID NO: 23), LGIPEQEYSCVVKMPSG (SEQ ID NO: 24), EQLGIPEQEY (SEQ ID NO: 25), QLGIPEQEY (SEQ ID NO: 26), LGIPEQEYSCVVKMPS (SEQ ID NO: 27), LGIPEQEYSCVVKMP (SEQ ID NO: 28), LGIPEQEYSCVVKM (SEQ ID NO: 29), LGIPEQEYSCVV (SEQ ID NO: 30), LGIPEQEYSCV (SEQ ID NO: 31), LGIPEQEYSC (SEQ ID NO: 32), QLGIPEQEYSC (SEQ ID NO: 33), LGIPEQEYS (SEQ ID NO: 34) that have one or more amino acid substitutions and combinations of the additional $NH_2$ and COOH termini amino acids that flank LGIPEQEY (SEQ ID NO: 1) with one or more amino acid substitutions and a cell-permeable sequence such as R9 (SEQ ID NO: 13).

Replication defective viral expression vectors (e.g., lentivirus, adenovirus, adeno-associated virus, herpes virus, and others) capable of expressing the peptides disclosed herein are also suitable delivery systems.

DETAILED DESCRIPTION

Figure 1:
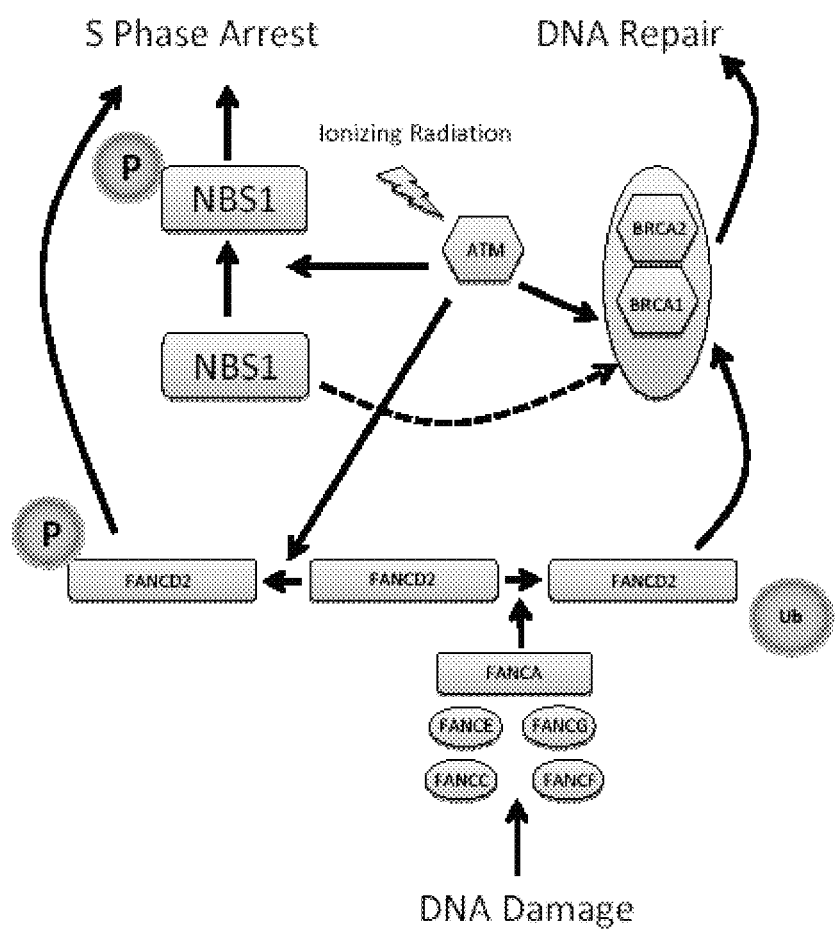
FIG. 1 illustrates a strategy behind the use of caPCNA peptides to induce cell death in cancer cells. Mechanisms of caPCNA peptide in inhibiting PCNA action in cells without a critical DNA repair protein, BRCA1. caPCNA peptides are more effective in cells lacking BRCA1. When mutated BRCA1 is present in tumors, they are often resistant to treatment by DNA damaging agents like chemotherapy. Loss of BRCA1 often leads to aggressive tumors; however, the tumorcells are more sensitive to DNA damaging agents because they lack this DNA repair protein.

Chemotherapeutic strategies are designed to exploit differences between malignant versus nonmalignant cell biology with the overall goal being selective inhibition of cancerous cells. Since, in many cases, cancer cells rapidly proliferate in comparison to nonmalignant cells, they also exhibit an increase in (often erroneous) DNA repair processes. There are numerous examples of drugs in the clinic that either induce DNA damage or inhibit DNA damage repair processes in malignant cells.

Chemotherapeutic agents such irradiation, doxorubicin, cisplatin, and the like can be nonspecific, resulting in deleterious side effects in patients. Without being bound by theory, it is believed herein that caPCNA peptides represent a novel strategy aimed at targeting caPCNA, a cancer-associated isoform on which malignant cells rely for DNA replication and repair processes.

The approximate $IC_{50}$s of the caPCNA peptide and its alanine-substituted derivatives, P129A and Q131A, have been determined in HCC1937 and HCC1937+wild-type BRCA1 breast cancer cells. The ability of the caPCNA peptides to enhance the cytotoxic effects of DNA damaging agents is described herein. A reduction of the $IC_{50}$ for cisplatin in the presence of caPCNA peptides is discovered herein.

Lower doses of chemotherapeutic agents needed to kill cancer cells (reduce toxicity to patients without compromising efficacy) and increase sensitivity to chemotherapy in drug-resistant cells are useful in treating various cancer types.

Methods and compositions disclosed herein relate to caPCNA-peptide variants, peptidomimetics, functional analogs thereof that selectively disrupt vital cellular functions in cancer cells. There are at least two modes of actions of these peptides. For example, caPCNA-derived peptide variants either compete with caPCNA to bind to caPCNA-interacting proteins or alternatively bind to a site on caPCNA-interacting protein that disrupts the interaction.

Without being bound by theory, it is believed herein that specific peptide variants derived from the caPCNA protein sequence are able to block the binding of one or more cellular proteins that participate in DNA replication, repair, cell cycle control, apoptosis, transcription, or chromosomal recombination in cancer cells. The binding of caPCNA to these cellular proteins is disrupted when caPCNA derived peptides are allowed to compete with these proteins for their naturally occurring binding site on PCNA. By disrupting the naturally occurring interaction between PCNA and the proteins that bind to or interact with PCNA, normal cellular functions that recruit PCNA are disrupted. This disruption of vital cellular machinery renders the caPCNA-derived peptide variants cytotoxic by themselves or in combination with other molecules, such as, for example cancer chemotherapeutic drugs. These peptides, either alone or in combination with other cancer therapy agents, are useful cancer chemotherapeutics or augmentors of the pharmacodynamic effect of specific anti-cancer chemotherapeutics. The peptide inhibitors disclosed herein sensitize tumor cells towards chemotherapy agents that damage DNA and also render tumors that are generally resistant to cancer drugs more responsive to treatments.

The term "sensitize" as used herein, for therapeutic purposes, generally refers to the ability of the peptides disclosed herein to lower the amount of a growth inhibitory agent or a cytotoxic agent (e.g., cisplatin, doxorubicin, and the like) needed to kill 50% of a group of cancer cells (e.g., a tumor) within a defined period of time (e.g., 24, 48, 72 hours).

The terms "pre-cancerous" or "pre-malignant" generally refer to a condition which may or may not be recognizable as a morphological change in tissue architecture that is known to be, or thought to be, associated with the development of a cancer within that tissue (organ). In addition, the initial molecular changes in gene expression, (or expression of specific isoforms of proteins), known to be associated with some percentage of cancer cells that are found in tumor tissues, may precede readily discernable morphological changes within the cells of these tissues undergoing the cancer transformation process. Thus the initial changes in the expression patterns of specific genes and/or proteins may be the first events associated with the molecular transformation process leading to the development of a cancer; may only be recognizable at the molecular level, as they have not in themselves induced an alteration in the morphology of the cells, and/or tissue, to the extent that it can be recognized by a trained individual (pathologist) at the light microscopic level.

The term "augment" or "augmenting" as used herein, for therapeutic purposes, generally refers to an improvement in the pharmacodynamic effect (referred to as the efficacy) of a therapeutic agent. Thus, the term "augment" refers to the ability of the peptide to raise the efficacy of a therapeutic agent (e.g., cisplatin, doxorubicin, and the like) leading to the killing of a greater number of cancer cells over the same unit of time (e.g., 24, 48, or 72 hour period) when the peptide is administered prior to, along with, or after the therapeutic agent as compared to the therapeutic agent alone.

Peptide variants derived from the protein Proliferating Cell Nuclear Antigen (PCNA) are identified herein that have the ability to act, in conjunction with DNA damaging agents (e.g., cisplatin, doxorubicin, and the like), to enhance the therapeutic effects of such agents to treat a variety of cancer cells. Without being bound by theory, it is believed herein that the modes of action of caPCNA-based peptide inhibitors and their roles in inhibiting cancer proliferation in the presence of a DNA damaging agent is by inhibiting the interaction between caPCNA and one or more DNA repair proteins, thereby inhibiting the repair of damaged DNA. The peptides are derived from the amino acid sequence within PCNA, for example, encompassing amino acids 126-133 and include one or amino acid mutations.

caPCNA-derived peptide variants and peptidomimetics represent novel anti-cancer therapeutic agents and also augment or sensitize tumor cells towards existing cancer therapies.

Without being bound by theory, it is believed that the peptide sequences disclosed herein target a region of the caPCNA protein that is likely to be uniquely unfolded in cancer cells. Thus, the peptides disclosed herein are designed to selectively target tumor cells by virtue of their ability to compete with caPCNA for regulating the activity of specific proteins interacting with the amino acid sequences within PCNA that are involved in at least one of the following cellular processes: DNA replication, repair, recombination, transcription, cell cycle checkpoint control, and apoptosis.

The peptides disclosed herein may be synthesized using standard peptide synthesis procedures and equipments or can be obtained commercially (e.g., United Biochemical Research Co., Seattle Wash.). A caPCNA-derived peptide that includes amino acids 126-133 of the human PCNA molecule (LGIPEQEY (SEQ ID NO: 1)) having at least one amino acid substitution, followed by a cell penetrating peptide (CPP) sequence, e.g., a polyarginine sequence to facilitate uptake of the peptide into cells selectively inhibits cancer cells in vitro.

In certain embodiments involving in vitro methodologies, uptake of caPCNA peptide variants were initiated by incubation of this peptide with the cancer cells in the presence of dimethyl sulfoxide (DMSO) in either phosphate buffered saline (PBS) or culture media containing 0.2-2% DMSO, without serum for about 4-24 hours. Uptake of these peptides is also efficiently mediated by encapsulation of the peptide in a liposome formulation and subsequent incubation with the cancer cells at 37° C. for about 4-24 hours. These peptides also augment the cytotoxic effects of chemotherapeutic agents such as doxorubicin, cisplatin, and the like.

The term "agent" as used herein includes nucleic acids, proteins, protein fragments, peptides, synthetic peptides, peptidomimetics, analogs thereof, small molecules, inhibitors, and any chemical, organic or bioorganic molecule capable of affecting protein-protein interaction or a cellular process.

The terms "caPCNA peptide variants" or "peptide variants" mean peptides whose sequences were derived from caPCNA and include one or more mutations such as substitution mutations or deletion mutations or amino acid analogs or a combination thereof. For example, LGIPEQEY (SEQ ID NO: 1) representing amino acids 126-133 of PCNA is caPCNA derived sequence in which for example, amino acids G, P, Q, and penultimate E can be substituted with an amino acid such as alanine (A). Thus, $LX_1IX_2EX_3X_4Y$ (SEQ ID NO: 35) is a peptide variant wherein $X_{1-4}$ can be substituted either independently or collectively. In an embodiment, $X_1$ is A, $X_2$ is P, $X_3$ is Q, and $X_4$ is E. In another embodiment, $X_1$ is G, $X_2$ is A, $X_3$ is Q, and $X_4$ is E. In another embodiment, $X_1$ is G, $X_2$ is P, $X_3$ is A, and $X_4$ is E. In another embodiment, $X_1$ is G, $X_2$ is P, $X_3$ is Q, and $X_4$ is A. In another embodiment, $X_1$ is G, $X_2$ is A, $X_3$ is A, and $X_4$ is A. The "caPCNA peptide variants" or "peptide variants" can range from about 5-10, 5-50, 7-50, 8-20, 8-25, 8-30, 8-40, 8-50 amino acids in length. For example, the "caPCNA peptide variants" or "peptide variants" may consist essentially of about 5, 6, 7, 8, 9, 10, 11, 12, 13, 14, 15, 16, 17, 18, 19, 20, 25, 30, 35, 40, 45, or 50 contiguous amino acids from caPCNA wherein one or more amino acids are substituted. The "caPCNA peptide variants" or "peptide variants" may further comprise peptide translocation domains or sequences that enable the "caPCNA peptide variants" or "peptide variants" to penetrate or translocate across cellular membranes. The "caPCNA peptide variants" or "peptide variants" are also be modified to affect their lipophilicity to enhance peptide delivery into cancer cells. The peptides can be synthesized ("synthetic peptides") or can also be produced through recombinant techniques ("recombinant peptides") or expressed in vivo using gene expression techniques. These peptides can also be engineered to increase their in vivo stability (e.g., increase peptide stability by rendering them protease resistant) without significantly affecting their efficacy in inhibiting caPCNA-protein interactions. Mutations including insertions, deletions, substitutions, amino acid modifications that substantially do not affect the inhibitory activity of the peptides disclosed herein are within the scope. Peptides that consist essentially of the 126-133 sequence LGIPEQEY (SEQ ID NO: 1) having one or more mutations may include other heterologous sequences that do not materially affect the inhibitory function of the peptide variants disclosed herein.

The peptides disclosed herein show specificity for killing malignant cells compared to non-cancerous cells. For example, the peptides disclosed herein are substantially specific in which the peptides preferentially kill malignant cancer cells more than 50%, preferably more than 60% or 70% or 80% or 90% or 95% when compared to non-malignant cells.

A "peptide variant" or "peptide derivative" also refers to a molecule having an amino acid sequence of a region that is similar to a portion of PCNA or of a PCNA homolog, but additionally having at least one chemical modification of one or more of its amino acid side groups, α-carbon atoms, terminal amino group, or terminal carboxylic acid group. A chemical modification includes additional chemical moieties, creation of new bonds, and/or removal of chemical moieties. Modifications at amino acid side groups include acylation of lysine, ε-amino groups, N-alkylation of arginine, histidine, or lysine, alkylation of glutamic or aspartic carboxylic acid groups, and deamidation of glutamine or asparagine. Modifications of the terminal amino include the des-amino, N-lower alkyl, N-di-lower alkyl, and N-acyl modifications. Modifications of the terminal carboxy group include the amide, lower alkyl amide, dialkyl amide, and lower alkyl ester modifications. A lower alkyl is a C1-C4 alkyl. Furthermore, one or more side groups, or terminal groups, may be protected by protective groups known to the ordinarily-skilled protein chemist. The α-carbon of an amino acid may be mono-or di-methylated.

Those of skill in the art recognize that peptides may be substantially similar to the peptides described above in that an amino acid residue may be substituted with another amino acid residue having a similar side chain without substantially affecting the inhibitory functions of the peptide variants disclosed herein. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acid substitution groups include: valine-leucine-isoleucine, phenylalanine-tyrosine, lysine-arginine, alanine-valine, and asparagine-glutamine. Thus, the peptide inhibitors disclosed herein may have one or more conservative amino acid substitutions without substantially affecting the inhibitory functions of the peptide.

Non-naturally occurring variants of the caPCNA-derived peptides can readily be generated using recombinant techniques or chemical synthesis. Such variants include, but are not limited to deletions, additions and substitutions in the amino acid sequence of the disclosed peptides. For example, one class of substitutions is conserved amino acid substitution. Such substitutions are those that substitute a given amino acid in the disclosed caPCNA-derived peptides by another amino acid of like characteristics. Typically accepted as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. A list of possible amino acid substitutions is provided in Table 5 herein.

The term "variant" refers to a peptide having an amino acid sequence that differs to some extent from a native sequence peptide, that is, an amino acid sequence that varies from the native sequence by conservative amino acid substitutions, whereby one or more amino acids are substituted by another with same characteristics and conformational roles. The amino acid sequence variants possess substitutions, deletions, and/or insertions at certain positions within the amino acid sequence of the native amino acid sequence.

The PCNA-derived peptide variants can also be fused or otherwise linked to a ligand for a cell surface receptor that is present in cancer cells. The ligand is optionally cleavable such that the peptide variants (inhibitors) are targeted to a tumor cells using a tumor-specific ligand but are cleaved by a protease present in the tumor environment such that the peptide variants are free to enter the tumor cells. For example, the human transferrin receptor (hTfR), a marker for cellular proliferation is used as a target for therapeutics and is expressed at least 100-fold more in oral, liver, pancreatic, prostate, and other cancers (Lee et al., (2001) "Receptor mediated uptake of peptides that bind the human transferrin receptor" Eur. J. Biochem., 268: 2004-2012). Peptides, HAIYPRH (SEQ ID NO: 36) and THRPPM-WSPVWP (SEQ ID NO: 37) bind specifically hTfR and these peptides were able to target associated macromolecule to the hTfR (Lee, supra). These peptides bind sites that do not overlap with the native ligand, Tf, and are useful in vivo for targeting macromolecules to the endocytic pathway in hTfR-positive cells (Lee, supra). Such peptides can also be used to target PCNA-derived peptides to enhance peptide delivery and also to further enhance specific delivery.

The term "cell permeable factor" or "cell membrane carrier" or "cell penetrating element" refers to any component, including peptides, that enhance the ability of the peptide variants disclosed herein to translocate the cell membrane as long as the factor does not substantially affect the ability of the peptide variants to inhibit caPCNA interaction. Optionally, the cell-permeable factors operate through a non-endocytic and non-degradative pathway in mammalian cells. These factors may include cell penetrating peptides (CPP) or cell permeable peptides. Illustrative examples of suitable cell-permeable peptides or peptide domains to link or fuse caPCNA-derived peptides include small polybasic peptides derived from the transduction domains of certain proteins, such as polyarginine (R6-R21), the third-helix of the Antennapedia (Antp) homeodomain, an RYIRS (SEQ ID NO: 38) tag sequence, and those listed in Table 4 herein.

In an embodiment, the cell membrane permeable carrier is a peptide, preferably an arginine rich peptide. (see e.g., Futaki S. et al., (2001) "Arginine-rich peptides. An abundant source of membrane-permeable peptides having potential as carriers for intracellular protein delivery" J. Biol. Chem., 276, 5836). The number of arginine residues in a cell membrane permeable carrier peptide may contain more than 6 arginines, preferably 7, 8, 9, 10, 11, 12, 13, 14, or 15 arginine residues. The arginine residues in an arginine rich peptide need not be contiguous. One or more of the arginine residues may be a D-isomer of arginine. Those of skill in the art know how to select an appropriate arginine rich peptide with a suitable number of arginine residues.

A peptide hairpin can also be used to make use of the increased number of extracellular proteases surrounding tumor tissues (see U.S. patent application publication 20070041904, incorporated herein by reference) to deliver the inhibitors ("cargo") disclosed herein. The construct includes a polyarginine peptide covalently attached to a polyanionic segment, which would only be substantially internalized upon proteolytic cleavage of the anionic domain. Because the protease targeted is likely overexpressed on cancerous cells, internalization is more likely with the tumor cells compared to a normal cell. Cellular association of cell-penetrating peptides (CPPs) (e.g., polyarginine based) is blocked when they are fused to an inhibitory domain made up of negatively charged residues. Such fusions termed as activatable CPPs (ACPPs) because cleavage of the linker between the polycationic and polyanionic domains, usually by a protease, releases the CPP portion and its attached peptide of interest ("cargo") to bind to and enter cells such as tumor cells.

Pretreatment of the cell with a polycation, cationic polymer and/or cationic peptide before transportation of the heterologous compound into the cell is also useful (see e.g., 20060083737, incorporated herein by reference).

Nuclear localization sequences (NLS) for example, VQRKRQKLMP (SEQ ID NO: 39), SKKKKIKV (SEQ ID NO: 40), and GRKRKKRT (SEQ ID NO: 41) are also useful in transporting the peptide variants disclosed herein into tumor cells. Other NLS can be obtained for example at Nair et al., (2003), NLSdb: database of nuclear localization signals, Nucl. Acids Res., 31:397-399 (see also <http://cubic.bioc.columbia.edu/db/NLSdb/>).

In some embodiments, the peptide variants disclosed herein are conjugated to the cell membrane permeable carrier, optionally including a spacer. For example, a polyarginine peptide having 5-9 arginine residues may optionally include a non-arginine-based spacer peptide or a spacer having non-standard amino acids or amino acid analogs. The spacers generally provide additional length to minimize for example steric hindrance to the function or transport of the peptide variants disclosed herein. Spacers may include about 1, 2, 3, 4, 5, 6, 7, 8, 9, 10, 15 or more amino acids. Suitable amino acids for use as spacers include, for example, glycine.

The caPCNA peptide variants and the cell-permeable peptides are linked by chemical coupling in any suitable manner known in the art as long as rendering the conjugated proteins are biologically active. In an aspect, one way to increase coupling specificity is to directly chemical couple to a functional group found only once or a few times in one or both of the polypeptides to be cross-linked. For example, in many proteins, cysteine, which is the only protein amino acid containing a thiol group, occurs only a few times. Also, for example, if a polypeptide contains no lysine residues, a cross-linking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity. Alternatively, synthetic peptides with a modified residue can be synthesized such that specificity of linking is enhanced.

Cysteine residues may be replaced when they occur in parts of a polypeptide sequence where their participation in a cross-linking reaction would otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. When a cysteine residue is introduced, introduction at or near the amino or carboxy terminus is preferred. Conventional methods are available for such amino acid sequence modifications, whether the polypeptide of interest is produced by chemical synthesis or expression of recombinant DNA.

Coupling of the two constituents can be performed through a coupling or conjugating agent. Suitable intermolecular cross-linking reagents include for example, J-succinimidyl 3-(2-pyridyldithio) propionate (SPDP) or N,N'-(1, 3-phenylene)bismaleimide (both of which are highly specific for sulfhydryl groups and form irreversible linkages); N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents include: p,p'-difluoro-m,m'-dinitrodiphenylsulfon-e (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Cross-linking reagents may be homobifunctional, i.e., two functional groups that have the same reaction. A suitable homobifunctional cross-linking reagent is bismaleimidohexane ("BMH"). Cross-linking reagents may also be heterobifunctional. Heterobifunctional cross-linking agents have two different functional groups, for example an amine-reactive group and a thiol-reactive group, that will cross-link two proteins having free amines and thiols, respectively. Examples of heterobifunctional cross-linking agents are succinimidyl 4-(N-maleimidomethyl)cyclohexane-1-carboxylate ("SMCC"), m-maleimidobenzoyl-N-hydroxysuccinimide ester ("MBS"), and succinimide 4-(p-maleimidophenyl)butyrate ("SMPB"), an extended chain analog of MBS. The succinimidyl group of these cross-linkers reacts with a primary amine, and the thiol-reactive maleimide forms a covalent bond with the thiol of a cysteine residue. A hydrophilic moiety, such as a sulfonate group, may be added to the cross-linking reagent to improve its water solubility. Sulfo-MBS and sulfo-SMCC are examples of cross-linking reagents modified for water solubility.

Many cross-linking reagents yield a conjugate that may be non-cleavable under cellular conditions. However, some cross-linking reagents contain a covalent bond, such as a disulfide, that is cleavable under cellular conditions. For example, Traut's reagent, dithiobis (succinimidylpropionate) ("DSP"), and N-succinimidyl 3-(2-pyridyldithio)propionate ("SPDP") are well-known cleavable cross-linkers. The use of a cleavable cross-linking reagent permits the cargo moiety to separate from the transport polypeptide after delivery into the target cell. Direct disulfide linkage may also be useful.

Numerous cross-linking reagents, including the ones discussed above, are commercially available. Detailed instructions for their use are readily available from the commercial suppliers. A general reference on protein cross-linking and conjugate preparation is: Wong, Chemistry of protein conjugation and cross-linking, CRC Press (1991).

Chemical cross-linking may include the use of spacer arms. Spacer arms provide intramolecular flexibility or adjust intramolecular distances between conjugated moieties and thereby may help preserve biological activity. A spacer arm may be in the form of a polypeptide moiety that includes spacer amino acids, e.g. proline. Alternatively, a spacer arm may be part of the cross-linking reagent, such as in "long-chain SPDP" (Pierce Chem. Co., Rockford, Ill., Cat. No. 21651 H).

Alternatively, the chimeric peptide can be produced as a fusion peptide that includes the cell-permeable sequence and the caPCNA peptide variant sequence that can be expressed in known suitable host cells for large-scale production and purification. Fusion peptides, as described herein, can be formed and used in ways analogous to or readily adaptable from standard recombinant DNA techniques, as described above.

Native peptides (in L-form) may be subject to degradation by natural proteases, the peptides disclosed herein may be prepared to include D-forms and/or "retro-inverso isomers" of the peptide. In this case, retro-inverso isomers of short fragments and variants of the peptide of caPCNA peptide variants disclosed herein are prepared. The caPCNA peptide variants can have one or more L-amino acids, D-amino acids, or combinations of both. For example, in various embodiments, the peptides are D retro-inverso peptides. The term "retro-inverso isomer" refers to an isomer of a linear peptide in which the direction of the sequence is reversed and the chirality of each amino acid residue is inverted. See, e.g., Jameson et al., Nature, 368, 744-746 (1994); Brady et al., Nature, 368, 692-693 (1994). The overall result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence may be made into a D retro-inverso peptide by synthesizing a reverse of the sequence for the corresponding native L-amino acid sequence.

Suitable chemotherapy agents include for example, cyclophosphamide (CYTOXAN™), capecitabine (XELODA™), chlorambucil (LEUKERAN™), melphalan (ALKERAN™), methotrexate (RHEUMATREX™), cytarabine (CYTOSAR-U™), fludarabine (FLUDARA™), 6-mercaptopurine (PURINETHOL™), 5-fluorouracil (ADRUCIL™), paclitaxel (TAXOL™), docetal, abraxane, doxorubicin (ADRIAMYCIN™), irinotecan (CAMPTOSAR™), cisplatin (PLATINOL™), carboplatin (PARAPLATIN™), oxaliplatin, tamoxifen (NOLVADEX™), bicalutamide (CASODEX™), anastrozole (ARIMIDEX™), examestane, letrozole, imatinib (GLEEVEC™), rituximab (RITUXAN™), trastuzumab (HERCEPTIN™), gemtuzumab, ozogamicin, interferon-alpha, tretinoin (RETIN-A™, AVITA™, RENOVA™), arsenic trioxide, bevicizumab (AVASTIN™), bortezombi (VELCADE™), cetuximab (ERBITUX™), erlotinib (TARCEVA™), gefitinib (IRESSA™), gemcitabine (GEMZAR™), lenalidomide (REVLIMID™), Serafinib, Sunitinib (SUTENT™), panitumumab (VECTIBIX™), pegaspargase (ONCASPAR™), and Tositumomab (BEXXAR™) and prodrugs or precursors or combinations thereof.

Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

In an embodiment, the dosage of chemotherapy agents, when used in conjunction with the peptides of the disclosure, may be lower than the dosage used for a monotherapy. For example, doxorubicin, cisplatin, and the like, when coadministered (either before or during or after) with caPCNA peptides described herein, the dosage may be lowered by 25% or 35% or 50% or 60% or 75% or 80% of the standard dose. Depending on other factors, dosage may range from 300 mg/m$^2$ to 500 mg/m$^2$. Other suitable doses may be lower e.g., 20 mg/m$^2$, 50 mg/m$^2$, 100 mg/m$^2$, 150 mg/m$^2$, or 200 mg/m$^2$ or higher 400 mg/m$^2$, 450 mg/m$^2$, 500 mg/m$^2$, 550 mg/m$^2$, or 600 mg/m$^2$.

The peptides disclosed herein are also suitable for cancer patients undergoing radiotherapy (including all forms of ionizing radiations that are DNA damaging) and any other forms of cancer therapy. The amount of radiation used in radiation therapy is measured in gray (Gy), and may vary depending on the type and stage of cancer being treated. For curative cases, a typical dose for a solid epithelial tumor ranges from about 60 to 80 Gy, while lymphoma tumors are treated with about 20 to 40 Gy. Preventative (adjuvant) doses of radiation are typically around 45-60 Gy in 1.8-2 Gy fractions (e.g., for breast, head and neck cancers respectively.) Many other factors are considered by radiation oncologists when selecting a dose, including whether the patient is receiving chemotherapy or any other therapy, whether radiation therapy is being administered before or after surgery, and the degree of success of surgery. A typical fractionation schedule for adults is about 1.8 to 2 or to about 3 Gy per day. If the peptides of the present invention are used in combination with radiotherapy, then the radiation doses may reduced by, for example, 10%, 20%, 30%, 40%, 50%, 60%, and 75%. Modes of delivering radiotherapy include for example, conventional external beam radiotherapy (2DXRT), 3-dimensional conformal radiotherapy (3DCRT), stereotactic radiotherapy, image-guided radiation therapy (IGRT), and intensity-modulated radiation therapy (IMRT).

Particle therapy (Proton therapy) that uses energetic ionizing particles (protons or carbon ions) is also suitable. Radioisotope therapy (RIT) includes the use of radioisotopes to target tumor tissues. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu.

Radioimmunotherapy includes the use of biologicals such as antibodies and a radioisotope. Ibritumomab tiuxetan (ZEVALIN™) is a monoclonal antibody anti-CD20 conjugated to a molecule of Yttrium-90. Tositumomab Iodine-131 (BEXXAR™) is a molecule of Iodine-131 linked to the monoclonal antibody anti-CD20.

The peptide inhibitors disclosed herein are suitable augmenting agents that can be administered either prior to, during, and after administering a particular cancer therapy, e.g., chemotherapy or radiotherapy.

A "small molecule" refers herein to have a molecular weight below about 500 Daltons.

It is to be understood that cancers suitable for treatment using the peptides disclosed herein include, but are not limited to, malignancies such as various forms of glioblastoma, glioma, astrocytoma, meningioma, neuroblastoma, retinoblastoma, melanoma, colon carcinoma, lung carcinoma, adenocarcinoma, cervical carcinoma, ovarian carcinoma, bladder carcinoma, lymphoblastoma, leukemia, osteosarcoma, breast carcinoma, hepatoma, nephroma, adrenal carcinoma, or prostate carcinoma, esophageal carcinoma. If a malignant cell expresses a caPCNA isoform, the compositions disclosed herein are capable of disrupting the interaction of caPCNA isoform with one or more proteins. Metastases of cancers are also treated by the peptide inhibitors disclosed herein. Any cell, whether cancerous or premalignant or precancerous, if it expresses cancer specific PCNA isoform, is suitable for reducing cellular proliferation or chemoprevention.

Non-peptidic compounds that mimic peptide sequences are known in the art (Meli et al. *J. Med. Chem.*, 49:7721-7730 (2006), that describes methods of identifying nonpeptide small molecule mimics). Synthesis of non-peptide compounds that mimic peptide sequences is also known in the art (see, e.g., Eldred et al. *J. Med. Chem.*, 37:3882, (1994); Ku et al. J. Med. Chem., 38:9, (1995); Meli et al. *J. Med. Chem.*, 49:7721-7730 (2006)). Such nonpeptide compounds that mimic caPCNA-derived peptides or variants thereof disclosed herein that bind caPCNA are contemplated by the present invention.

The term "peptidomimetic" or "peptide mimetic" refers to a chemical compound having small protein-like chain (peptide) that includes non-peptidic elements such as non-natural amino acids. Peptidomimetics are designed and synthesized with the purpose of binding to target proteins in order to induce or effect a particular change. Generally, a peptidomimetic functions by mimicking or antagonizing key interactions of the parent peptide structure that it was designed to mimic or antagonize. A peptidomimetic normally does not have classical peptide characteristics such as enzymatically cleavable peptidic bonds. For a general review of the various techniques available for design and synthesis peptide mimetics, see al-Obeidi et al., (1998), "Peptide and peptidomimetic libraries. Molecular diversity and drug design" *Mol. Biotechnol.;* 9(3):205-23; and Houben-Weyl: Synthesis of Peptides and Peptidomemetics, Thieme Medical Publishers, 4$^{th}$ edition (2003).

As used herein, the terms "peptide mimetic," "peptidomimetic," and "peptide analog" are used interchangeably and refer to a synthetic chemical compound that has substantially the same structural and/or functional characteristics of caPCNA peptides or variants thereof disclosed herein. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or inhibitory or binding activity. Routine experimentation will determine whether a mimetic is within the scope of the disclosure, i.e., that its structure and/or function is not substantially altered. Thus, a mimetic composition is within the scope if it is capable of specifically inhibiting caPCNA-mediated cellular proliferation or cell death.

Polypeptide mimetic compositions can contain any combination of normatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like.

A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N=dicyclohexylcarbodiimide (DCC) or N,N=diisopropylcarbodiimide (DIC) Linking groups that can be an alternative to the traditional amide bond ("peptide bond") linkages include, e.g., ketomethylene (e.g., —C=O—$CH_2$— for —C=O—NH—), aminomethylene ($CH_2$—NH), ethylene, olefin (CH=CH), ether (—$CH_2$—O), thioether ($CH_2$—S), tetrazole ($CN_4$), thiazole, retroamide, thioamide, or ester (see, e.g., Spatola (1983) in Chemistry and Biochemistry of Amino Acids, Peptides and Proteins, Vol. 7, pp 267-357, A Peptide Backbone Modifications, Marcell Dekker, NY).

A polypeptide can also be characterized as a mimetic by containing all or some non-natural residues in place of naturally occurring amino acid residues. Normatural residues are well described in the scientific and patent literature; a few exemplary nonnatural compositions useful as mimetics of natural amino acid residues.

In another embodiment, peptides capable of disrupting caPCNA interaction include peptides of amino acid sequences with one or more amino acid substitutions that include about +3 contiguous or non contiguous additional amino acids on the $NH_2$ terminus of LGIPEQEY (SEQ ID NO: 1) and about +9 contiguous or non contiguous amino acids on the COOH terminus of LGIPEQEY (SEQ ID NO: 1). For example, some of these peptides include amino acid sequences of QLGIPEQEYSC (SEQ ID NO: 21) (+1-NH2 terminus, +2-COOH terminus), VEQLGIPEQEY (SEQ ID NO: 22) (+3-NH2 terminus), LGIPEQEYSCVVK (SEQ ID NO: 23) (+5-COOH terminus), LGIPEQEYSCVVKMPSG (SEQ ID NO: 24) (+9-COOH terminus), EQLGIPEQEY (SEQ ID NO: 25) (+2-NH2 terminus), QLGIPEQEY (SEQ ID NO: 26) (+1-NH2 terminus), LGIPEQEYSCVVKMPS (SEQ ID NO: 27) (+8-COOH terminus), LGIPEQEYSCVVKMP (SEQ ID NO: 28) (+7-COOH terminus), LGIPEQEYSCVVKM (SEQ ID NO: 29) (+6-COOH terminus), LGIPEQEYSCVV (SEQ ID NO: 30) (+4-COOH terminus), LGIPEQEYSCV (SEQ ID NO: 31) (+3-COOH terminus), LGIPEQEYSC (SEQ ID NO: 32) (+2-COOH terminus), QLGIPEQEYSC (SEQ ID NO: 33) (+1-NH2 terminus, +2-COOH terminus), LGIPEQEYS (SEQ ID NO: 34) (+1-COOH terminus) and combinations of the additional $NH_2$ and COOH termini amino acids that flank LGIPEQEY (SEQ ID NO: 1). Amino acid mutations including substitutions that do not affect the specificity of the peptides to generate csPCNA specific antibodies are within the scope of this disclosure. One or more of the amino acid residues in the peptides may be replaced with an amino acid analog or an unnatural or non-standard amino acid.

Dosage of the caPCNA-derived peptide variants depend on the efficacy of the peptides, stability of the peptides in vivo, mode of administration, the nature of cancer being treated, body weight, age of the patient and other factors that are commonly considered by a skilled artisan. For example, dosage of caPCNA-derived peptide variants drug can range from about 0.1-10.0 microgram (mcg)/kg body weight or from about 0.2-1.0 mcg/kg body weight or from about 0.5-5.0 mcg/kg body weight or from about 10.0-50.0 mcg/kg body weight. Depending on the toxicity effects and tumor killing capability, the dosage can also range from about 1.0-10.0 mg/kg body weight and from about 0.1-1.0 mg/kg body weight. The amount of the inhibitor that is administered to the subject can and will vary depending upon the type of inhibitor, the subject, and the particular mode of administration. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

Administration of the compositions disclosed herein may be via any route known to be effective by the physician of ordinary skill. Parenteral routes include intravenous, intramuscular, subcutaneous, and intraperitoneal routes of administration. Intravenous, intramuscular, and subcutaneous routes of administration of the compositions disclosed herein are suitable. For parenteral administration, the peptides disclosed herein can be combined with phosphate buffered saline (PBS) or any suitable pyrogen-free pharmaceutical grade buffer that meets FDA standard for human subject administration. As used herein, "pharmaceutically acceptable carrier" includes any and all solvents, diluents, or other liquid vehicle, dispersion or suspension aids, surface active agents, isotonic agents, thickening or emulsifying agents, preservatives and the like, as suited to the particular dosage form desired. Remington's Pharmaceutical Sciences, $20^{th}$ Edition, A. R. Gennaro (Williams and Wilkins, Baltimore, Md., 2000) discloses various carriers used in formulating pharmaceutical compositions and known techniques for the preparation thereof. Solutions or suspensions of the compositions described herein can also include a sterile diluent, such as water for injection, saline solution, fixed oils, polyethylene glycols, glycerine, propyleneglycol or other synthetic solvents; chelating agents, such as EDTA; buffers, such as acetates, citrates or phosphates; and agents for the adjustment of tonicity, such as sodium chloride or dextrose. A parenteral preparation of the compositions can be enclosed in ampoules, disposable syringes or multiple dose vials made of glass or plastic, in accordance with standard practice in the field. The compositions disclosed herein can be stored as a lyophilized sterile powder in vials containing for reconstitution and the unreconstituted product may be stored at −20° C.

Agents administered parenterally, i.e., intravenously, intramuscularly, etc., may include a sterile diluent such as water, saline solution, a pharmaceutically acceptable polyol such as glycerol, propylene glycol, polyethylene glycols, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the solution may be adjusted with acids or bases such as hydrochloric acid or sodium hydroxide. Preparations for oral administration generally include an inert diluent or an edible carrier. They may be include a pharmaceutically compatible binding agent such as microcrystalline cellulose, gum tragacanth or gelatin; an excipient such as starch or lactose; a disintegrating agent such as alginic acid, Primogel, or corn starch; a lubricant such as magnesium stearate or sterotes; a glidant such as colloidal silicon dioxide; a sweetening agent such as sucrose or saccharin; and/or a flavoring agent such as peppermint, methyl salicylate, or citrus flavoring. Oral preparations may be enclosed in gelatin capsules, compressed into tablets, or prepared as a fluid carrier. For administration by inhalation, the agent is generally delivered in the form of an aerosol spray from a pressurized container or dispenser that contains a suitable propellant, e.g., a gas such as carbon dioxide, or a nebulizer. For topical (e.g., transdermal or transmucosal) administration, penetrants appropriate to the barrier to be permeated are generally included in the preparation. Transmucosal administration may be accomplished through the use of nasal sprays or suppositories, and transdermal administration may be via ointments, salves, gels, patches, or creams as generally known in the art.

Peptides and other compositions disclosed herein can be administered via any suitable means. For example, the peptide compositions may be diluted in saline or any suitable buffer and administered directly intravenously. For example, the peptide compositions can be encapsulated in liposomes and administered intravenously of by any suitable method. For example, the peptide compositions can be delivered by an extended release drug delivery system known to one of ordinary skill in the art. Other modes of targeting tumors are also suitable. For example, U.S. patent application publication US20050008572 (Prokop et al.,) discloses methods and compositions relating to nanoparticular tumor targeting and therapy, the disclosure of which is hereby incorporated by reference. U.S. patent application publication US20030212031 (Huang et al.,) discloses stable lipid-comprising drug delivery complexes and methods for their production, the disclosure of which is hereby incorporated by reference.

Replication defective viral expression vectors (e.g., lentivirus; adenovirus, adeno-associated virus, herpes virus, and others) capable of expressing the peptides disclosed herein are also suitable delivery systems. Other nucleic acid delivery systems such as retroviral vectors, adenovirus vectors, adeno-associated virus vectors, alphavirus vectors, Semliki Forest virus-based vectors, Sindbis virus-based vectors are also useful, See, Schlesinger and Dubensky (1999) *Curr. Opin. Biotechnol.* 5:434-439 and Ying et al. (1999) *Nat. Med.* 5(7):823-827.

caPCNA-derived peptides disclosed herein are expressed from a suitable viral vector. cDNA sequence of PCNA gene is found for example, in Travali et al., (1989), *J. Biol. Chem.* 264 (13), 7466-7472, incorporated by reference and also in several GenBank entries such as for example, NM_002592 and NM_182649. Standard cloning methods based on PCR and site-directed mutagenesis techniques are used to engineer one or more Ala substitutions or other conserved mutations in the coding region of caPCNA regions for expressing the variant peptides in a cancer cell.

In addition, the term "pharmaceutically effective amount" or "therapeutically effective amount" refers to an amount (dose) effective in treating a patient, having, for example, breast cancer. For example, in vitro test conditions, a suitable dose would kill at least 50% of cancer cells. It is also to be understood herein that a "pharmaceutically effective amount" may be interpreted as an amount giving a desired therapeutic effect, either taken in one dose or in any dosage or route, taken alone or in combination with other therapeutic agents. In the case of the present disclosure, a "pharmaceutically effective amount" may be understood as an amount of caPCNA-derived peptide variants which may for example, suppress (e.g., totally or partially) the interaction of caPCNA and one or more of its interacting partners, or reduce tumor growth, or reduce cancer cell proliferation.

Administration of caPCNA peptides induces cell death in cancerous cells and augments the beneficial effects of chemotherapeutics. caPCNA peptides are particularly effective in cells harboring mutations in DNA repair proteins, for example, BRCA1.

While the invention is susceptible to various modifications and alternative forms, specific embodiments will herein be described in detail. It should be understood, however, that there is no intent to limit the invention to the particular forms described, but on the contrary, the intention is to cover all modifications, equivalents, and alternatives falling within the spirit and scope of the invention.

EXAMPLES

Example. The cytotoxic effects of cell-permeable caPCNA-derived peptide variants on breast cancer cells harboring BRCA1 mutations were examined. caPCNA peptides are discovered herein to be effective in cancer cells harboring mutations in DNA repair proteins. Inhibiting DNA repair proteins represents a viable target for anti-cancer therapy. For example, inhibitors of a DNA repair protein Poly (ADP-ribose) polymerase family, member I, (PARP1) are used as anti-cancer therapeutic agents. caPCNA peptides that selectively interact with caPCNA isoform in malignant or pre-malignant cells are useful either as a monotherapy or a combination therapy with one or more chemotherapy agents such as cisplatin.

Breast cancer cells were obtained from a patient harboring a hereditary mutation in BRCA1, a major component of DNA double strand break repair (HCC1937 cells). HCC1937 is a near-tetraploid cell line from mammary gland whose cells are homozygous for a frameshift mutation in BRCA1. The cell line is available at ATCC.

As a genetically matched control, wild-type BRCA1 has been transduced into HCC1937 cells (referred to as HCC1937+wild-type BRCA1). HCC1937+wild-type BRCA1 cells were selected for maintenance of the vector using 1 µg/mL puromycin. All cells in these assays were used at passage numbers <25.

MTT [3-(4,5-dimethylthiazol-2-yl)-2,5-diphenyltetrazolium bromide] assays were conducted with caPCNA peptides at a variety of time points both alone and in combination with a DNA damaging agent e.g., cisplatin in HCC1937 and HCC1937+wild-type BRCA1 cells. The MTT assay is based on the ability of a mitochondrial dehydrogenase enzyme from viable cells to cleave the tetrazolium rings of the pale yellow MTT dye and form dark blue formazan crystals. These formazan crystals are largely impermeable to cell membranes and thus accumulate within healthy cells. Solubilization of the cells by the addition of a detergent results in the liberation and solubilization of the crystals. The number of proliferating cells is directly proportional to the level of formazan product created. The color can then be quantified using a simple colorimetric assay. The results are read on a multiwall scanning spectrophotometer (ELISA reader). The peptides used in these experiments including caPCNA peptide, Q131A (LGIPEAEY (SEQ ID NO: 5)), and P129A (LGIAEQEY (SEQ ID NO: 3)) were ordered and obtained from Anaspec (Fremont, Calif.). ca PCNA peptide was dissolved in sterile 1×PBS solution to create a 1.5 mM stock concentration. caPCNA peptides with alanine substitutions (e.g., P129A (SEQ ID NO: 3) and Q131A (SEQ ID NO: 5)) were dissolved in sterile 1×PBS solution to create 1.0 mM stock solutions.

Cisplatin powder was dissolved in sterile 1×PBS to create a 3.3 mM stock solution. The stock peptide and cisplatin solutions were sterile filtered using a 0.2 µM filter, aliquoted, and stored at −20° C. until use in the MTT experiments.

MTT assays: The efficacy of caPCNA peptides (caPeptides) were tested using the MTT assays: HCC1937 and HCC137+wildtype BRCA1 cells were grown in DMEM 1× (supplemented with 10% fetal bovine serum and 5% penicillin/streptomycin) and were plated at a densities of $5.5×10^3$ or $7×10^3$, respectively, in 96 well plates (100 µL total volume per well) and allowed to attach overnight in a 37° C. incubator (5% $CO_2$). Then, caPCNA peptide stock solution was diluted to final working concentrations in DMEM 1× (10% fetal bovine serum and 5% penicillin/streptomycin) of 150 µM, 100 µM, 75 µM, 50 µM, and 25 µM. Media was removed from cells and replaced with media containing caPCNA peptide at various concentrations (200 µL total volume per well). Cells were cultured with caPCNA peptide-containing media for 24, 48 or 72 hours. At the appropriate treatment timepoint, 20 µL MTT (5 mg/mL in PBS) reagent was added to each well and plates were incubated for an additional 4 hours. Media/dye solution was then aspirated and 200 µL DMSO was added to each well. Plates were rocked at room temperature for five minutes to dissolve crystals and transferred to an ELISA plate reader. Absorbance was measured at 550 nm. The extent to which caPeptides inhibited cell proliferation was calculated as a percentage of the absorbance in each well containing caPCNA peptide relative to wells containing no caPCNA peptide (negative control) for both HCC1937 and HCC1937+ wild-type BRCA1 cells.

The negative control wells were assigned a value of 100%. The data were derived from a total of 3 experiments done at 24 and 48 hour timepoints and two experiments done at the 72 hour timepoint. The data shown here are representative of results obtained in each cell line at these timepoints.

Efficacy of P129A (SEQ ID NO: 3) and Q131A (SEQ ID NO: 5) caPCNA peptides: Cells were cultured and plated in 96 well plates as described herein. P129A (SEQ ID NO: 3) or Q131A (SEQ ID NO: 5) stock solution was diluted to final working concentrations in DMEM 1× (10% fetal bovine serum and 5% penicillin/streptomycin) of 100 µM, 75 µM, 50 µM, 25 µM, and 12.5 µM. Media was removed from cells and replaced with media containing P129A (SEQ ID NO: 3) or Q131A (SEQ ID NO: 5) caPCNA peptides at various concentrations (200 µL total volume per well) and cells were cultured with peptide-containing media for 24 hours. After 24 hours, the MTT assay was completed and data analysis was performed as described herein.

Figure 2:
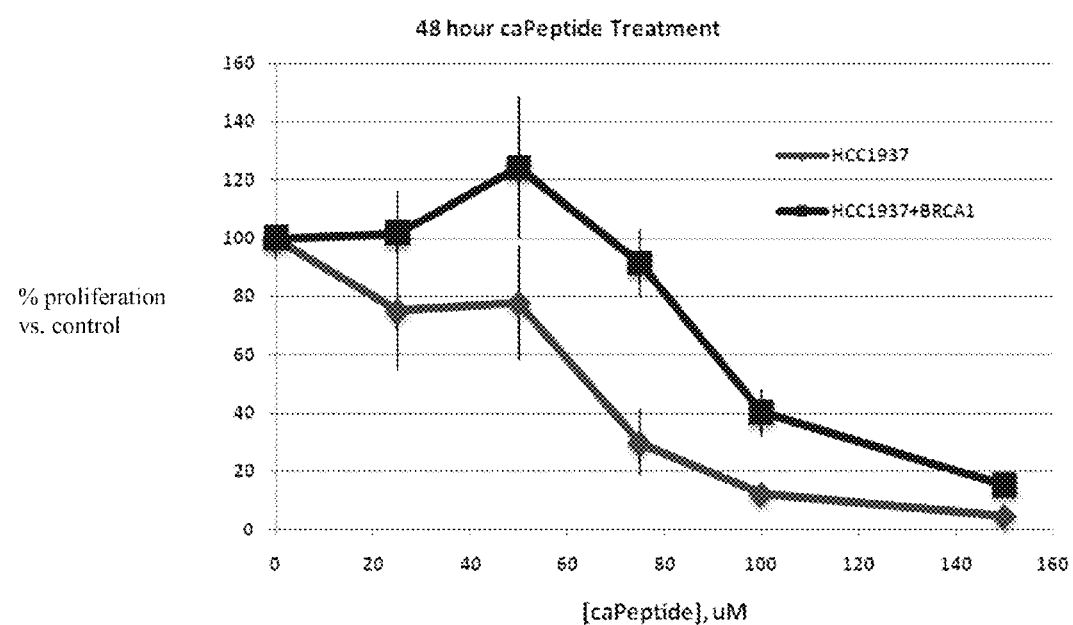
FIG. 2 shows BRCA negative cells are more sensitive to the cytotoxic action of caPCNA peptide.

Results: HCC1937 cells show a trend of increased sensitivity to caPCNA peptides at 24, 48, and 72 hour treatment timepoints in comparison to HCC1937+wild-type BRCA1 cells (FIG. 2). caPeptides with alanine substitutions at particular amino acid residues (P129A (SEQ ID NO: 3) and Q131A (SEQ ID NO: 5)) show enhanced efficacy in comparison to wild-type peptides, and Q131A appears to be more effective of these peptides tested.

CaPCNA peptide treatment inhibits colony formation in both HCC1937 and HCCI937+wild-type BRCA1 cells. This effect is more pronounced in HCC1937 cells lacking the wildtype BRCA1. These data suggest that peptides derived against a cancer-associated epitope of PCNA have anticancer uses, and are particularly effective in treatment of cancers harboring mutations in DNA repair proteins. In addition, these peptides are capable of acting synergistically (i.e., synergistic inhibition of tumor cells) with DNA damaging chemotherapeutics, for example, cisplatin and the like, to reduce the IC50 of these chemotherapeutic agents. caPCNA peptides therefore may reduce toxicity to patients without compromising treatment efficacy.

Example. The efficacy of caPCNA peptides used in combination with cisplatin on breast cancer cells harboring BRCA1 mutations was examined. The purpose of these experiments was to determine whether caPCNA peptides at a fixed concentration could lower the IC50 of cisplatin in HCC1937 and HCC1937+wild-type BRCA1 cells. Cells were cultured and plated in 96 well plates as described herein. Then, cisplatin stock solution was diluted to final working concentrations in DMEM 1× (10% fetal bovine serum and 5% penicillin/streptomycin) of 200 µM, 100 µM, 75 µM, 50 µM, 25 µM, and 12.5 µM. caPCNA peptide stock solution was diluted to final working concentrations in DMEM 1× (10% fetal bovine serum and 5% penicillin/streptomycin) of 60 µM or 25 uM. Media was removed from cells and replaced with media containing cisplatin alone, cisplatin and 60 µM caPCNA peptide added simultaneously, or 25 µM caPCNA peptide (pretreatment) followed by addition of cisplatin into the media at increasing concentrations after 3 or 6 hours. Cells treated with cisplatin alone or cisplatin plus 60 µM caPCNA peptide treatment were incubated with peptide and/or cisplatin containing media for both 24 and 48 hour timepoints. Cells treated with 25 µM caPCNA peptide pretreatment plus cisplatin were incubated with media containing caPCNA peptide and cisplatin for 24 hours. At the appropriate treatment timepoint, the MTT assay was completed and data analysis was performed as described herein. The data detailing the effects of cisplatin on these cell lines were derived from multiple experiments. The data showing the effects of cisplatin in combination with 60 µM of caPCNA peptide and cisplatin and 25 µM caPCNA peptide pretreatment was experimentally verified.

Clonogeizic survival assay: Clonogenic survival after caPCNA peptide treatment: The purpose of this experiment was to determine the effects of high caPCNA peptide treatment (100 µM caPCNA peptide for 48 hours) on ability of cells plated at low density to proliferate and form colonies. HCC1937 and HCC1937+wild-type BRCA1 cells were plated in 6-well plates and allowed to attach overnight at 37° C.

Then, media was removed and replaced with 100 µM caPCNA peptide in DMEM 1× (10% fetal bovine serum and 5% penicillin/streptomycin). Untreated cells were used as a negative control. Plates were incubated with media containing peptide for 48 hours. Live cells were then collected, counted, plated at low density (1×10 cells in 10 cm2 dishes) and allowed to grow in DMEM 1× (20% fetal bovine serum, 5% penicillin/streptomycin) for 13 days. After 13-day incubation, media was removed and plates were washed twice with 1×PBS. Cells were fixed with 70% EtOH for 10 minutes, dried, and stained for 1 hour with 20% Giemsa diluted in MilliQ water. Dye was removed; plates were rinsed, dried overnight and photographed. Images shown are representative of results obtained for treated and untreated HCC1937 and HCC1937+wild-type BRCA1 cells.

Figure 3A:
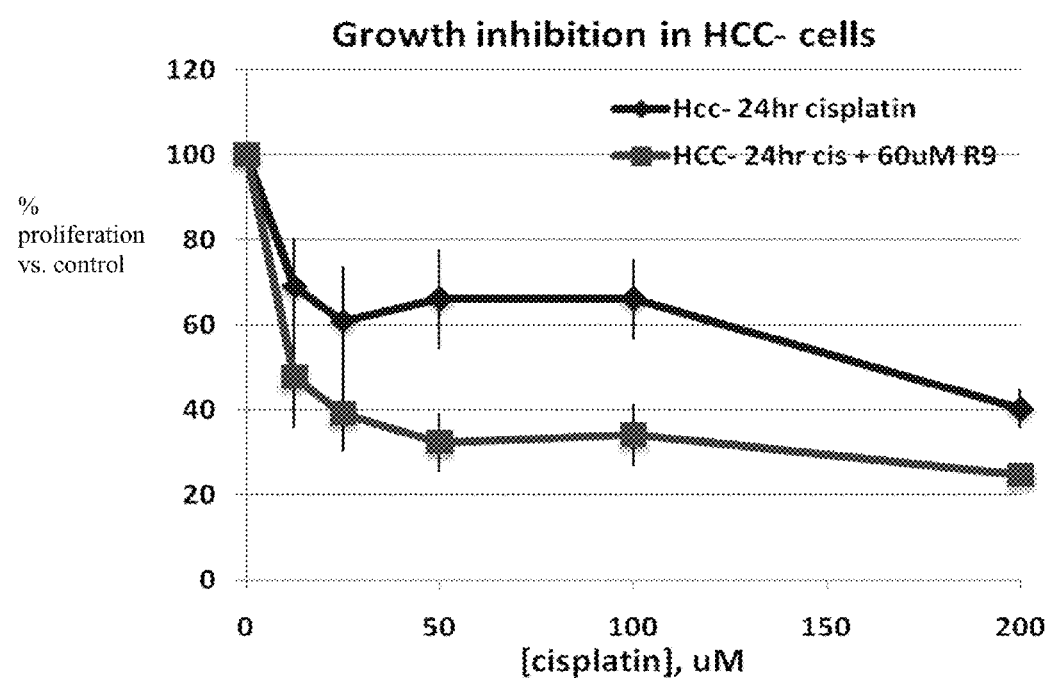
FIG. 3A shows growth inhibition in HCC1937 cells lacking BRCA1 (A) after 24-hr treatment with cisplatin or cisplatin plus R9-caPCNA peptide.
Figure 3B:
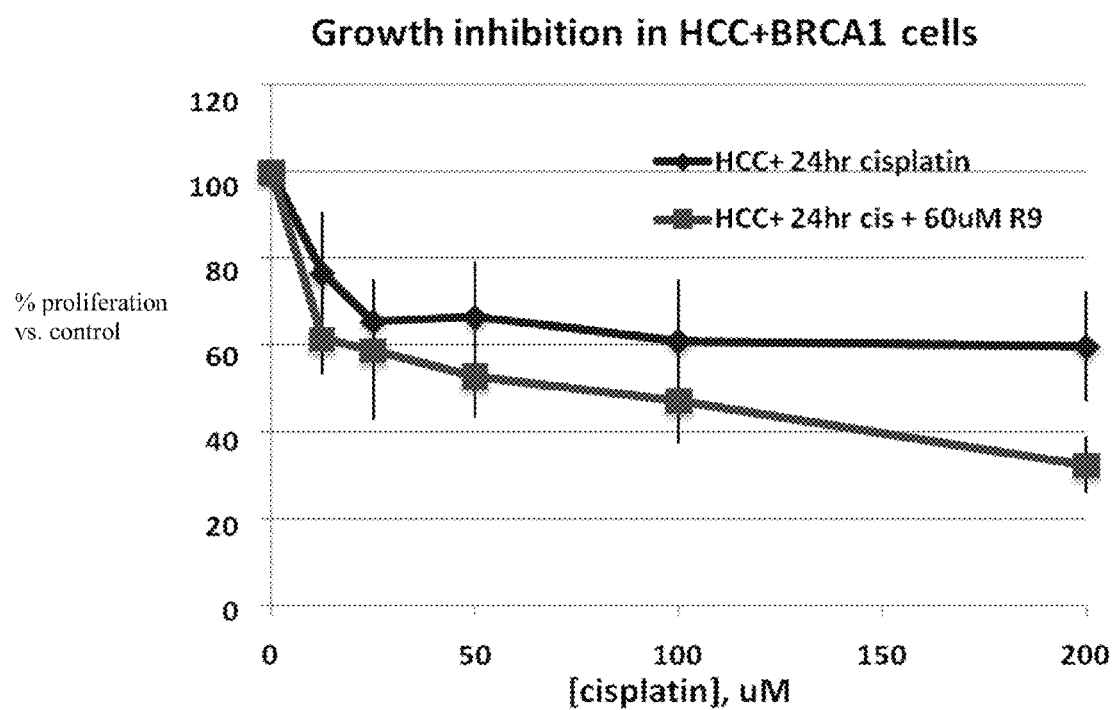
FIG. 3B shows growth inhibition in HCC1937 cells+ BRCA1 (B) after 24-hr treatment with cisplatin or cisplatin plus R9-caPCNA peptide.
Figure 4A:
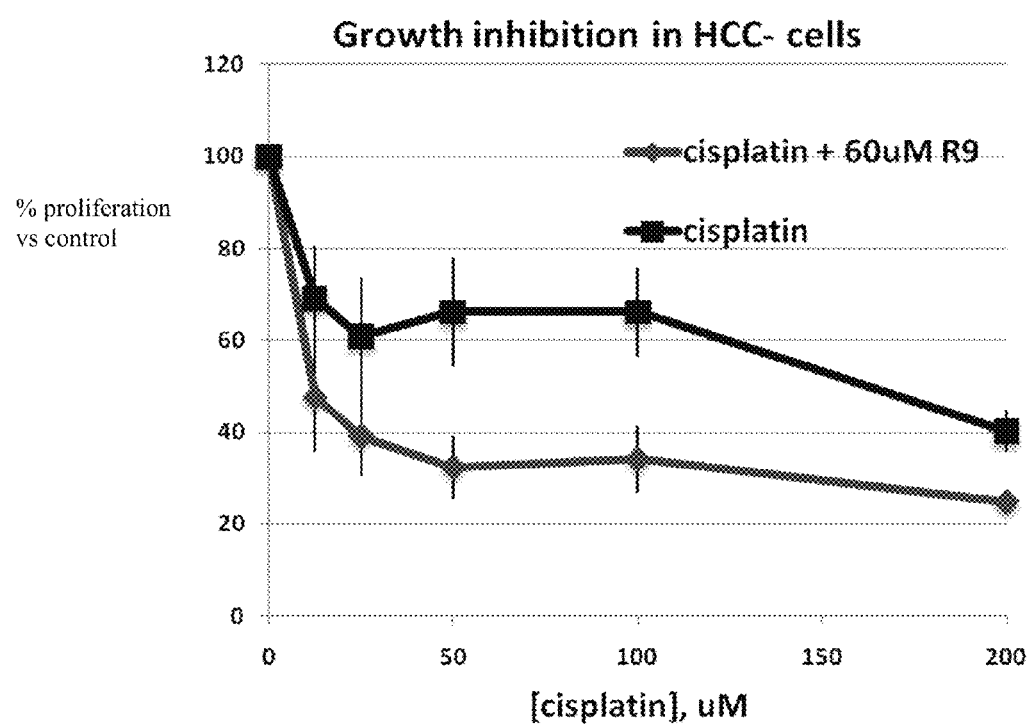
FIG. 4A shows R9-PCNA peptide lowers cisplatin dose needed for growth inhibition in HCC1937 cells lacking BRCA1, and is more effective in cells lacking BRCA1. In HCC1937 cells lacking BRCA1, the $IC_{50}$ value for R9-PCNA peptide (60 μM)+cisplatin is ~20 μM and the $IC_{50}$ value for cisplatin alone is ~155 μM.
Figure 4B:
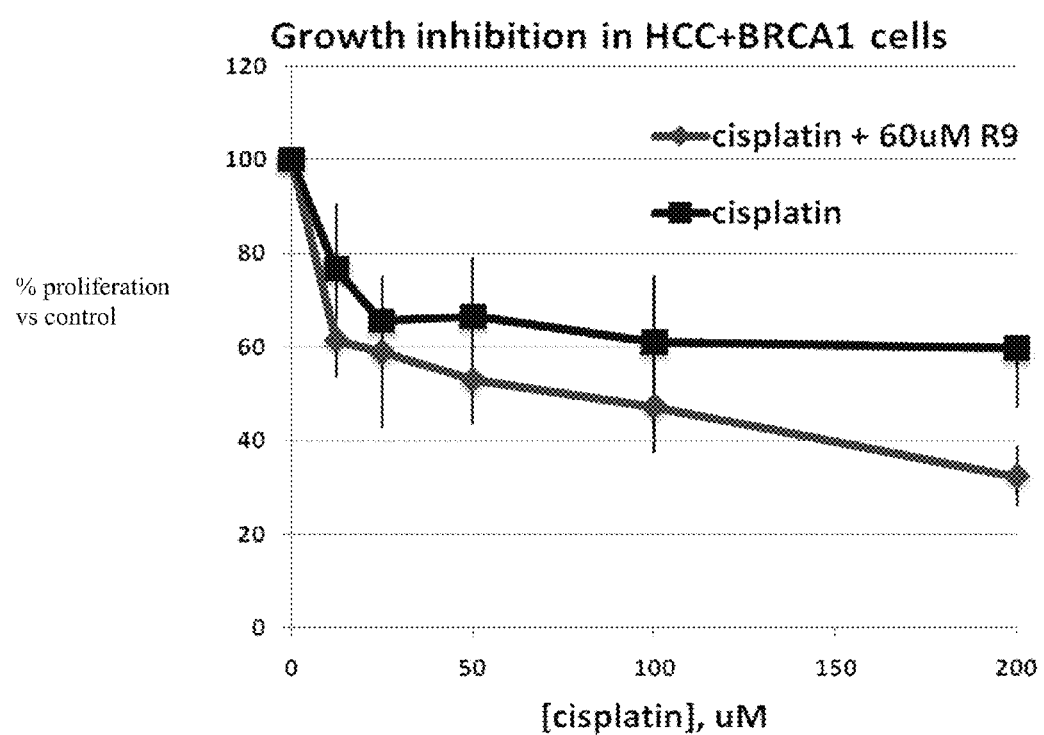
FIG. 4B shows R9-PCNA peptide lowers cisplatin dose needed for growth inhibition in HCC1937 cells with BRCA1. In HCC1937 cells with BRCA1 (B), the $IC_{50}$ value for R9-PCNA peptide (60 μM)+cisplatin is ~100 μM and the $IC_{50}$ value for cisplatin alone is >200 μM.
Figure 5A:
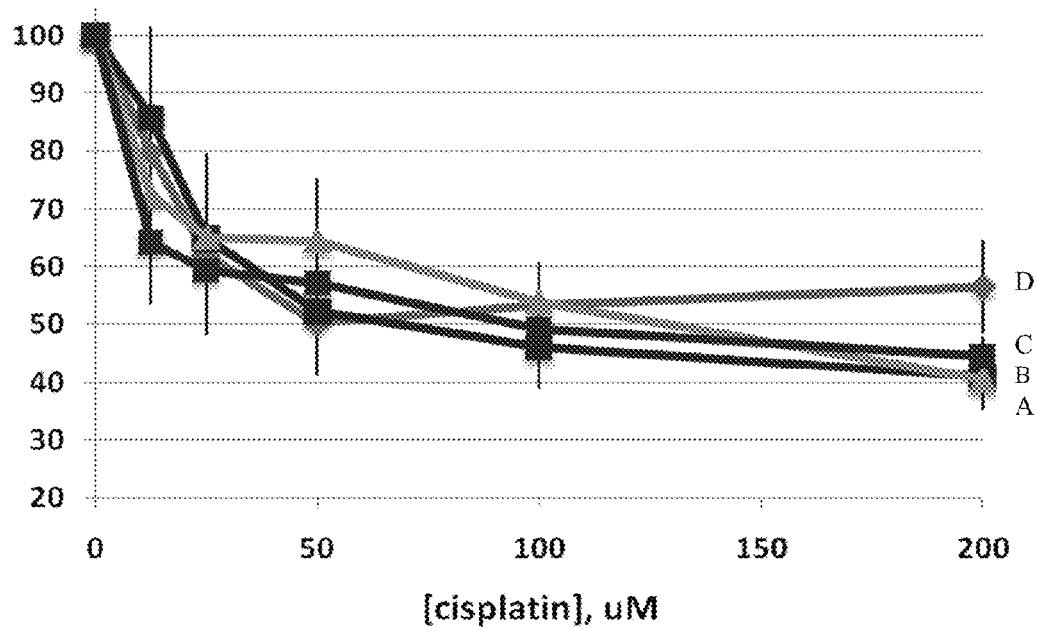
FIGS. 5A and 5B show that HCC1937 cells are more sensitive to cisplatin+caPCNA peptide combination treatment.
Figure 5B:
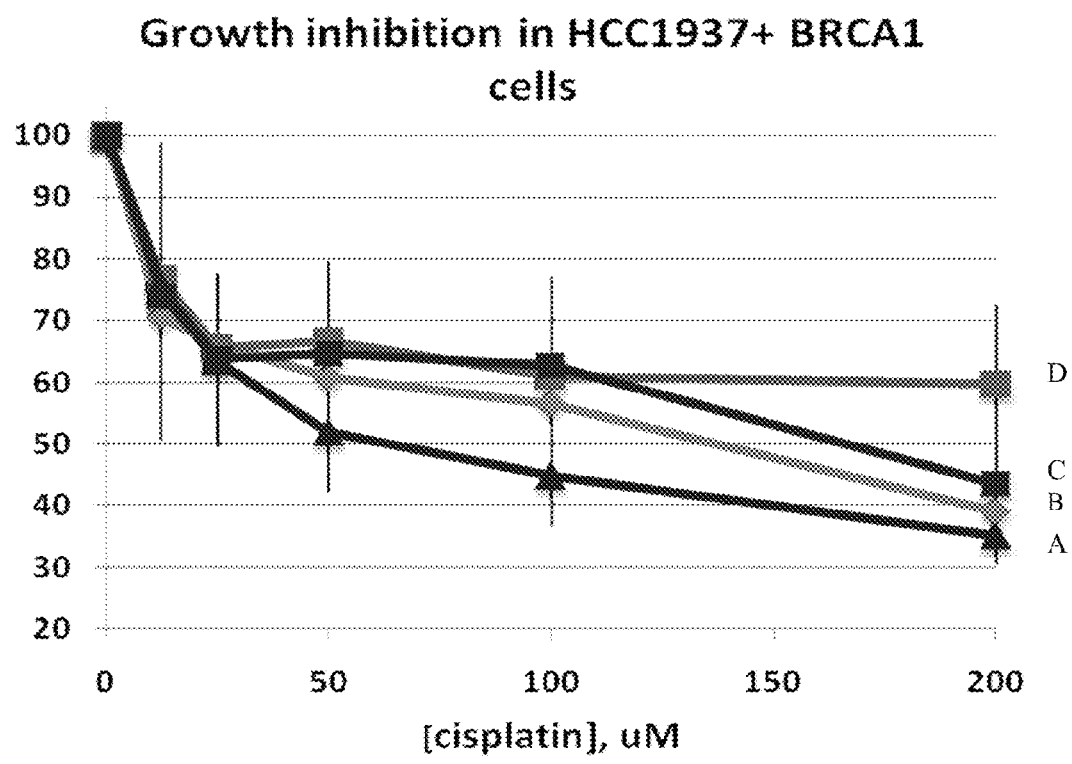
Figure 6A:
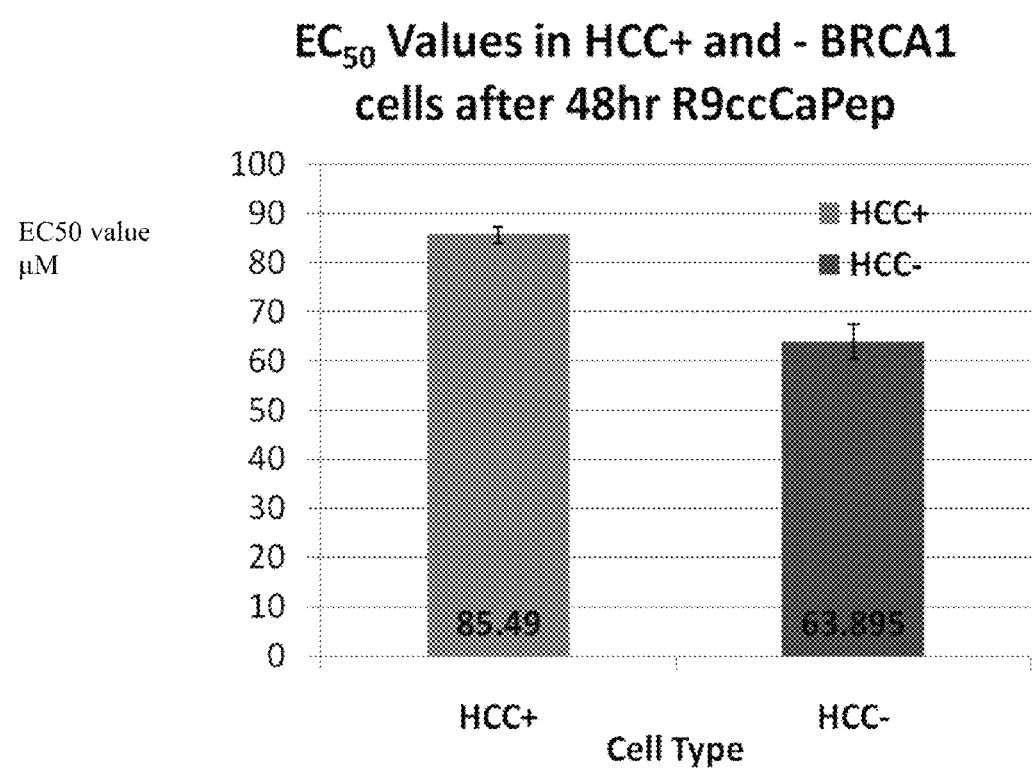
FIGS. 6A and 6B show a summary of a 48-hr timepoint for EC50 values involving caPCNA peptides and cisplatin for HCC+ and HCC− cells.
Figure 6B:
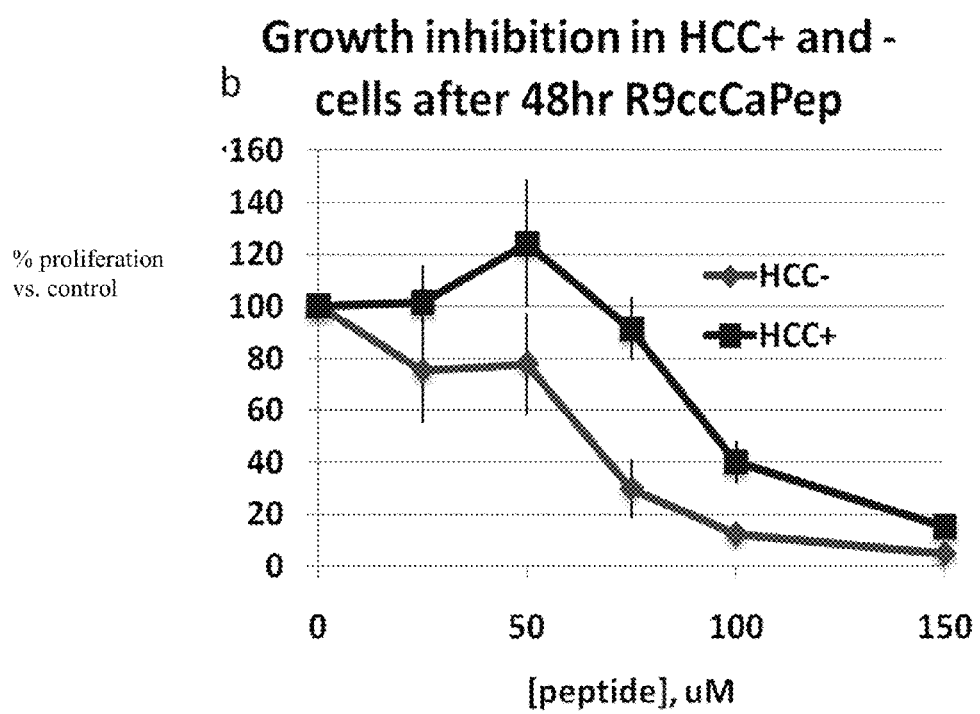

HCC1937 and HCC1937+wild-type BRCA1 cells are relatively resistant to the effects of cisplatin (FIG. 3A, 3B). 60 µM caPCNA peptide added simultaneously with cisplatin treatment lowered the IC50 of cisplatin and this effect was more pronounced in HCC1937 cells lacking wild-type BRCA1 (FIGS. 4A-B)

Therefore, the caPCNA-derived peptides or the variants disclosed herein present a viable chemopreventative option to reduce the overall occurrence of cancer in tissue types that are likely to express caPCNA isoform at an early stage. A practitioner or a clinician can readily determine if the individual or a tissue biopsy expresses caPCNA by using a caPCNA-specific detection method e.g., caPCNA-specific antibodies disclosed in international patent application publication WO2006/116631 or based on caPCNA isoform post-translational modifications disclosed in international patent application publication WO 2007/002574, the contents of both the publications are herein incorporated by reference in their entirety.

TABLE 1

Exemplary caPCNA peptide domains containing the amino acid 126-133 region.

PCNA Sequence 111-125 (SEQ ID NO: 42)
LVFEAPNQEK VSDYEMKLMD LDVEQLGIPEQEYSCVVKMP SGEFARICRD
LSHIGDAVVI SCAKDGVKFS ASGELGNGNI KLSQTSNVDK EEEAVTIEMN (SEQ ID NO: 43)

PCNA Sequence 118-135 (SEQ ID NO: 44)
LVFEAPNQEK VSDYEMKLMD LDVEQLGIPEQEYSCVVKMP SGEFARICRD
LSHIGDAVVI SCAKDGVKFS ASGELGNGNI KLSQTSNVDK EEEAVTIEMN (SEQ ID NO: 43)

TABLE 1 -continued

Exemplary caPCNA peptide domains containing the amino acid 126-133 region.

PCNA Sequence 121-133 (SEQ ID NO: 45)
LVFEAPNQEK VSDYEMKLMD LDVE<u>QLGIPEQEYS</u>CVVKMP SGEFARICRD
LSHIGDAVVI SCAKDGVKFS ASGELGNGNI KLSQTSNVDK EEEAVTIEMN (SEQ ID NO: 43)

PCNA Sequence 126-133 (SEQ ID NO: 1)
LVFEAPNQEK VSDYEMKLMD LDVEQ<u>LGIPEQEY</u>SCVVKMP SGEFARICRD
LSHIGDAVVI SCAKDGVKFS ASGELGNGNI KLSQTSNVDK EEEAVTIEMN (SEQ ID NO: 43)

PCNA Sequence 126-143 (SEQ ID NO: 46)
LVFEAPNQEK VSDYEMKLMD LDVEQ<u>LGIPEQEYSCVVKMP S</u>GEFARICRD
LSHIGDAVVI SCAKDGVKFS ASGELGNGNI KLSQTSNVDK EEEAVTIEMN (SEQ ID NO: 43)

PCNA Sequence 126-153 (SEQ ID NO: 47)
LVFEAPNQEK VSDYEMKLMD LDVEQ<u>LGIPEQEYSCVVKMP SGEFARICRD
LSHIGDAVVI S</u>CAKDGVKFS ASGELGNGNI KLSQTSNVDK EEEAVTIEMN (SEQ ID NO: 43)

PCNA Sequence 126-163 (SEQ ID NO: 48)
LVFEAPNQEK VSDYEMKLMD LDVEQ<u>LGIPEQEYSCVVKMP SGEFARICRD
LSHIGDAVVI SCAKDGVKFS</u> ASGELGNGNI KLSQTSNVDK EEEAVTIEMN (SEQ ID NO: 43)

The regions containing the 126-133 sequence are shown as underlined.

TABLE 2

Amino acid sequences of R9-lined caPCNA-derive peptides.

| Name | Sequence |
|---|---|
| R9 Alone | RRRRRRRRR (SEQ ID NO: 13) |
| caPeptide | LGIPEQEY (SEQ ID NO: 1) |
| R9-caPep | RRRRRRRRRCCLGIPEQEY (SEQ ID NO: 49) |
| R9-L126A | RRRRRRRRRCCAGIPEQEY (SEQ ID NO: 50) |
| R9-L127A | RRRRRRRRRCCLAIPEQEY (SEQ ID NO: 51) |
| R9-L128A | RRRRRRRRRCCLGAPEQEY (SEQ ID NO: 52) |
| R9-L129A | RRRRRRRRRCCLGIAEQEY (SEQ D NO: 53) |
| R9-L130A | RRRRRRRRRCCLGIPAQEY (SEQ ID NO: 54) |
| R9-L131A | RRRRRRRRRCCLGIPEAEY (SEQ ID NO: 55) |
| R9-L132A | RRRRRRRRRCCLGIPEQAY (SEQ ID NO: 56) |
| R9-L133A | RRRRRRRRRCCLGIPEQEA (SEQ ID NO: 57) |
| FITC-R9-caPep | FITC-RRRRRRRRRCCLGIPEQEY (SEQ ID NO: 49) |

TABLE 3

Cytotoxic effects of R9-linked caPCNA peptides.

| Peptide designation | Arginine-linked caPCNA peptide and the respective alanine substitutions | % cancer cell death |
|---|---|---|
| 126-133 peptide Unsub. Peptide (SEQ ID NO: 58) | 126-L G I P E Q E Y -133<br>R9- 1 2 3 4 5 6 7 8 | 43 ± 10 |
| A1-sub. Peptide (SEQ ID NO: 59) | R9- A 2 3 4 5 6 7 8 | 8 ± 9 |
| A2-sub. Peptide (SEQ ID NO: 60) | R9- 1 A 3 4 5 6 7 8 | 47 ± 13 |
| A3-sub. Peptide (SEQ ID NO: 61) | R9- 1 2 A 4 5 6 7 8 | 21 ± 12 |
| A4-sub. Peptide (SEQ ID NO: 62) | R9- 1 2 3 A 5 6 7 8 | 80 ± 7 |
| A5-sub. Peptide (SEQ ID NO: 63) | R9- 1 2 3 4 A 6 7 8 | 45 ± 14 |
| A6-sub. Peptide (SEQ ID NO: 64) | R9- 1 2 3 4 5 A 7 8 | 93 ± 7 |
| A7-sub. Peptide (SEQ ID NO: 65) | R9- 1 2 3 4 5 6 A 8 | 88 ± 4 |
| A8-sub. Peptide (SEQ ID NO: 66) | R9- 1 2 3 4 5 6 7 A | 7 ± 6 |
| Negative control | Scrambled peptide | 5 ± 4 |

R9 refers to a cell penetrating peptide that includes a polyarginine sequence e.g., nine contiguous arginine residues. Alanine substitutions in the caPCNA peptide affect its cytotoxic action. U937 cells were treated with each alanine substituted peptide and the scrambled peptide and % cell death evaluated by flow cytometry. The scrambled peptide and alanine substitutions at positions aa126 or aa133 show reduced cytotoxic activity. Substitutions at aa129, aa131, or aa132 cause an increase in cytotoxicity of the peptide. Substitutions that result in a neutral change include aa127 and aa130. Substitution at aa128 results in a decrease in cytotoxic action but not to the levels of aa126 or aa133.

TABLE 4

Cell permeable or cell-penetrating peptides

| Name | Peptide sequence | References (each is incorporated by reference in its entirety) |
|---|---|---|
| R9 | RRRRRRRRR (SEQ ID NO: 13) | |
| PENETRATIN ™ | RQIKIWFQNRRMKWKK (SEQ ID NO: 16) | U.S. Pat. No. 5,888,762 |
| Tat | GRKKRRQRRRPPQ (SEQ ID NO: 17) | U.S. Pat. Nos. 5,804,604 and 5,674,980 |

TABLE 4 -continued

Cell permeable or cell-penetrating peptides

| Name | Peptide sequence | References (each is incorporated by reference in its entirety) |
|---|---|---|
| TAT (47-57) | YGRKKRRQRRR (SEQ ID NO: 67) | Wender, PA. et al. Proc. Natl. Acad. Sci. USA 97, 13003 (2000) |
| Tat (48-57) | GRKKRRQRRR (SEQ ID NO: 19) | Hottiger, M. and G. Nabel, J. Virol. 72, 8252 (1998). |
| Tat (Npys) | YGRKKRRQRRRGGG-C(Npys)-NH2 (SEQ ID NO: 68) | |
| TRANSPORTAN ™ | GWTLNSAGYLLGKINLKALAALAKKIL (SEQ ID NO: 18) | |
| VP22 | DAATATRGRSAASRPTERPRAPARSASRPRRPVD (SEQ ID NO: 69) | WO 97/05265 |
| MAP | KLALKLALKALKAALKLA (SEQ ID NO: 70) | |
| KALA | WEAKLAKALAKALAKHLAKALAKALKACEA (SEQ ID NO: 71) | |
| ppTG20 | GLFRALLRLLRSLWRLLLRA (SEQ ID NO: 72) | |
| Trimer | VRLPPP (SEQ ID NO: 73) | |
| P1 | MGLGLHLLVLAAALQGAWSQPKKKRKV (SEQ ID NO: 74) | |
| MPG | GALFLGFLGAAGSTMGAWSQPKKKRKV (SEQ ID NO: 75) | |
| Pep-1 | KETWWETWWTEWSQPKKKRKV (SEQ ID NO: 76) | Fischer, R. et al. Chem. Bio. Chem. 6, 2126 (2005). |
| hCT | LGTYTQDFNKFHTFPQTAIGVGAP (SEQ ID NO: 77) | |
| C105Y | CSIPPEVKFNKPFVYLI (SEQ ID NO: 78) | Rhee and Davis, (2006) J. Biol. Chem. 281, 1233 |
| 105Y | SIPPEVKFNKPFVYLI (SEQ ID NO: 79) | Boland, K. et al. J. Biol. Chem. 270, 28022 (1995) |
| Lipid Membrane Translocating Peptide | KKAAAVLLPVLLAAP (SEQ ID NO: 80) and its D-isomer | |
| Nuclear localization | PKKKRKV (SEQ ID NO: 81) | |
| RVG | YTIWMPENPRPGTPCDIFTNSRGKRASNGGGG (SEQ ID NO: 82) | Kumar, P. et al. Nature 448, 39 (2007). |
| Transdermal Peptide | ACSSSPSKHCG (SEQ ID NO: 83) | Chen, Y. et al. Nat. Biotechnol. 24, 455 (2006). |
| Antennapedia Leader Peptide (CT) | KKWKMRRNQFWVKVQRG (SEQ ID NO: 84) | Kanovsky, M. et al. Proc. Natl. Acad. Sci. 98, 12438 (2001). |

TABLE 4 -continued

Cell permeable or cell-penetrating peptides

| Name | Peptide sequence | References (each is incorporated by reference in its entirety) |
|---|---|---|
| Antennapedia Peptide | RQIKIWFQNRRMKWKK (SEQ ID NO: 85) | Jain, M. et al. Cancer Res. 65, 7840 (2005). |
| SynB1 | RGGRLSYSRRRFSTSTGRA (SEQ ID NO: 86) | |

The peptides listed above can be synthesized or are commercially available (e.g., AnaSpec, San Jose, CA) with an $NH_2$ moiety for coupling with the peptide variants disclosed herein.

TABLE 5

List of exemplary amino acid conserved substitutions

| Amino Acid | Code | Conserved Substitutions |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ille, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4 or 5-phenylproline |
| Proline | P | D-Pro, L-1-thioazolidine-4-carboxylic acid, D- or L-1-oxazolidine-4-carboxylic acid |
| Serine | S | De-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

TABLE 6

Preferential killing of cancer cells by R9-caPeptide

| Cell line | % Dead Cells |
|---|---|
| MCF 10A (non-malignant) | 18.2 |
| MCF 7 (breast cancer) | 91.5 |

We Claim:

1. A method of inducing cell death in a breast cancer cell, a leukemia cell, or a premalignant breast cell having a mutation in a deoxyribonucleic acid (DNA) repair protein, the method comprising administering a therapeutically effective amount of a composition comprising a cancer-specific proliferating cell nuclear antigen (caPCNA) peptide molecule, wherein the caPCNA peptide molecule consists of the amino acid sequence LGIPEAEY (SEQ ID NO:5), wherein the composition further comprises one or more agent selected from the group consisting of a cell penetrating factor, a cell surface targeting factor and a nuclear localization sequence, and wherein the caPCNA peptide molecule is optionally attached to said one or more agent selected from the group consisting of a cell penetrating factor, a cell surface targeting factor and a nuclear localization sequence.

2. A method of reducing cellular proliferation of a breast cancer cell, a leukemia cell, or a pre-malignant breast cell of an individual having one or more mutations in a deoxyribonucleic acid (DNA) repair protein, the method comprising administering a therapeutically effective amount of a composition comprising a cancer-specific proliferating cell nuclear antigen (caPCNA) peptide molecule, wherein the caPCNA peptide molecule consists of the amino acid sequence LGIPEAEY (SEQ ID NO:5), wherein the composition further comprises one or more agent selected from the group consisting of a cell penetrating factor, a cell surface targeting factor and a nuclear localization sequence, and wherein the caPCNA peptide molecule is optionally attached to said one or more agent selected from the group consisting of a cell penetrating factor, a cell surface targeting factor and a nuclear localization sequence.

3. The method according to claim 1, wherein the deoxyribonucleic acid (DNA) repair protein participates in homologous recombination.

4. The method according to claim 1, wherein the DNA repair protein is selected from breast cancer 1, early onset (BRCA1), breast cancer 2, early onset (BRCA2), partner and localizer of BRCA2 (PALB2), RAD51, RAD52, XRCC3, MRE11, and any combination thereof.

5. The method according to claim 4, wherein the DNA repair protein is breast cancer 1, early onset (BRCA1).

6. The method according claim 1, wherein the cancer-specific proliferating cell nuclear antigen (caPCNA) peptide molecule is attached to a cell penetrating factor.

7. The method according to claim 6, wherein the cell penetrating factor is covalently attached or conjugated to the cancer-specific proliferating cell nuclear antigen (caPCNA) peptide molecule.

8. The method according to claim 6, wherein the cell penetrating factor is recombinantly fused to the cancer-specific proliferating cell nuclear antigen (caPCNA) peptide molecule.

9. The method according to claim 6, wherein the cell penetrating factor is a peptide is selected from the amino acid sequences RRRRRRR (SEQ ID NO: 11), RRRRRRRR (SEQ ID NO: 12), RRRRRRRRR (SEQ ID NO: 13), RRRRRRRRRR (SEQ ID NO: 14), RRRRRRRRRRR (SEQ ID NO: 15), RQIKIWFQNRRMKWKK (SEQ ID NO: 16), GRKKRRQRRRPPQ (SEQ ID NO: 17), GWTLNSAGYLLGKINLKALAALAKKIL (SEQ ID NO: 18), and GRKKRRQRRR (SEQ ID NO: 19).

10. The method according to claim 9, wherein the amino acid sequence comprises one or more amino acid's D-isomer.

11. The method according to claim 1, wherein the composition further comprises a cell surface targeting factor.

12. The method according to claim 1, wherein the composition further comprises a nuclear localization sequence.

13. The method according to claim 1, wherein the composition is administered intravenously.

14. The method according to claim 1, wherein the composition is delivered intratumorally.

15. The method according to claim 1, further comprising administering a chemotherapeutic agent selected from doxorubicin, irinotecan, cyclophosphamide, chlorambucil, melphalan, methotrexate, cytarabine, fludarabine, 6-mercaptopurine, 5-fluorouracil, capecytabine, cisplatin, carboplatin, oxaliplatin, and any combination thereof.

* * * * *